United States Patent
Gottimukkala et al.

(10) Patent No.: US 12,139,753 B2
(45) Date of Patent: Nov. 12, 2024

(54) METHODS FOR PARTNER AGNOSTIC GENE FUSION DETECTION

(71) Applicant: LIFE TECHNOLOGIES CORPORATION, Carlsbad, CA (US)

(72) Inventors: Rajesh Gottimukkala, Fremont, CA (US); Amir Marcovitz, Menlo Park, CA (US); Jeoffrey Schageman, Austin, TX (US); Varun Bagai, Austin, TX (US); Jian Gu, Austin, TX (US); James Veitch, Berkeley, CA (US); Kelli Bramlett, Austin, TX (US); Scott Myrand, Saline, MI (US); Fiona Hyland, San Mateo, CA (US); Seth Sadis, Ann Arbor, MI (US); Paul Williams, Ann Arbor, MI (US)

(73) Assignee: Life Technologies Corporation, Carlsbad, CA (US)

( * ) Notice: Subject to any disclaimer, the term of this patent is extended or adjusted under 35 U.S.C. 154(b) by 1164 days.

(21) Appl. No.: 16/825,238

(22) Filed: Mar. 20, 2020

(65) Prior Publication Data

US 2020/0318175 A1     Oct. 8, 2020

Related U.S. Application Data

(60) Provisional application No. 62/822,429, filed on Mar. 22, 2019.

(51) Int. Cl.

| | |
|---|---|
| *C12Q 1/68* | (2018.01) |
| *C12Q 1/6851* | (2018.01) |
| *G06F 17/18* | (2006.01) |
| *G16B 25/10* | (2019.01) |

(52) U.S. Cl.
CPC ........... *C12Q 1/6851* (2013.01); *G06F 17/18* (2013.01); *G16B 25/10* (2019.02)

(58) Field of Classification Search
None
See application file for complete search history.

(56) References Cited

U.S. PATENT DOCUMENTS

| | | |
|---|---|---|
| 2011/0065113 A1 | 3/2011 | Chinnaiyan et al. |
| 2016/0019340 A1 | 1/2016 | Gottimukkala et al. |

FOREIGN PATENT DOCUMENTS

| | | |
|---|---|---|
| CN | 102712953 A | 10/2012 |

OTHER PUBLICATIONS

Kalendar-Atak et al. (PLoS Genetics, 2013, 9(12):1-16) (Year: 2013).*
Wang et al. (Nature Biotechnology, 2009, 27(11):1005-1011) (Year: 2009).*
Magi-Galluzzi et al. (The Prostate 2011, 71:489-497). (Year: 2011).*
Hovelson et al. (Neoplasia, 2015, 17(4):385-399, with Supplemental Material p. 1-82) (Year: 2015).*
Blidner, et al: "Design, Optimization, and Multisite Evaluation of a Targeted Next-Generation Sequencing Assay System for Chimeric RNA5 from Gene Fusions and Exon-Skipping Events in Non-Small Cell Lung Cancer", The Journal of Molecular Diagnostics, vol. 21, No. 2, Mar. 1, 2019 (Mar.1, 2019), pp. 352-365, XP055700709, USISSN: 1525-1578, DOI: 10.1016/j.jmoldx.2018.10.003.
Lira, et al: "A Single-Tube Multiplexed Assay for Detecting ALK, ROS1, and RET Fusions in Lung Cancer", The Journal of Molecular Diagnostics, vol. 16, No. 2, Mar. 1, 2014 (Mar. 1, 2014), pp. 229-243, XP055280268, USISSN: 1525-1578, DOI: 10.1016/j.jmoldx.2013.11.007.
PCT/US2020/023850, International Search Report and Written Opinion, Jun. 22, 2020, 15 pages.
Vaughn, et al: "Simultaneous detection of lung fusions using a multiplex RT-PCR next generation sequencing-based approach: a multi-institutional research study", BMC Cancer, vol. 18, No. 1, Aug. 16, 2018 (Aug. 16, 2018), 8 pages, XP055520866, DOI: 10.1186/s12885-018-4736-4.
Olshen et al., "Circular Binary Segmentation for the Analysis of Array-Based DNA Copy Number Data", Biostatistics, vol. 5, No. 4, 2004, pp. 557-572.
Soda et al., "Identification of the Transforming EML4-ALK Fusion Gene in Non-Small-Cell Lung Cancer", Nature, vol. 448, Aug. 2, 2007, pp. 561-567, doi:10.1038/nature05945.
Lira M.E., et al., "Multiplexed Gene Expression and Fusion Transcript Analysis to Detect ALK Fusions in Lung Cancer," The Journal of Molecular Diagnostics, Jan. 1, 2013, vol. 15, No. 1, pp. 51-61.

* cited by examiner

*Primary Examiner* — Stephanie K Mummert
(74) *Attorney, Agent, or Firm* — Carolyn Koenig

(57) ABSTRACT

A method for detecting a gene fusion includes amplifying a nucleic acid sample in the presence of primer pool to produce a plurality of amplicons. The primer pool includes primers targeting a plurality of exon-exon junctions of a driver gene. The amplicons correspond to the exon-exon junctions. The amplicons are sequenced and aligned to a reference sequence. The number of reads corresponding to each amplicon is normalized to give a normalized read count. A baseline correction is applied to the normalized read counts for the amplicons to form corrected read counts. A binary segmentation score is calculated for each corrected read count. A predicted breakpoint for the gene fusion is determined based on the amplicon index corresponding to the maximum absolute binary segmentation score. Gene fusion events may be detected in a partner agnostic manner, i.e. without prior knowledge of the specific fusion partner genes or specific breakpoint information.

20 Claims, 24 Drawing Sheets

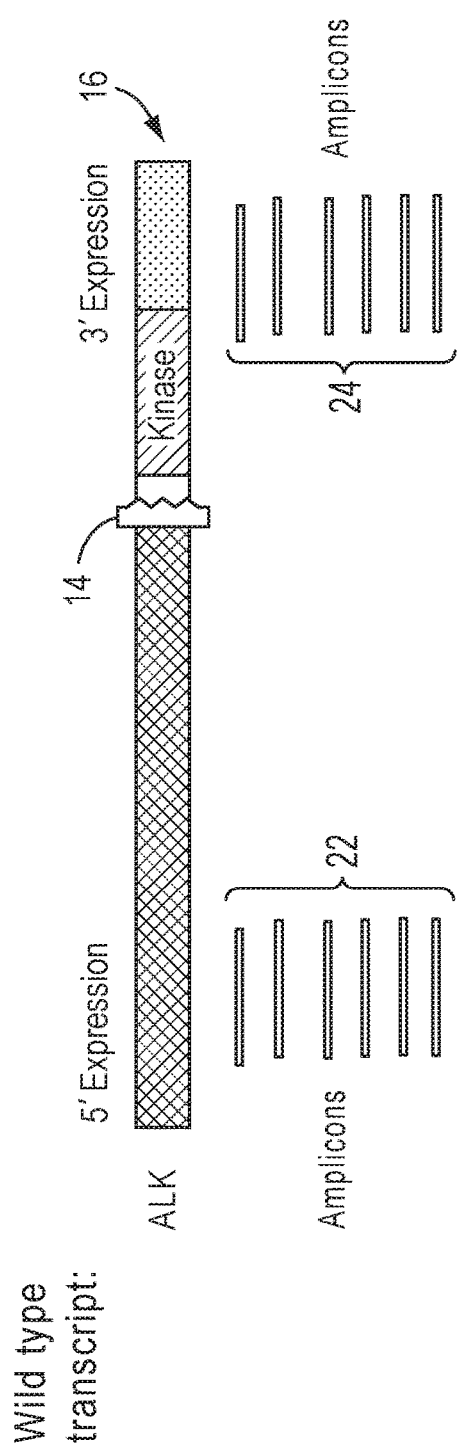
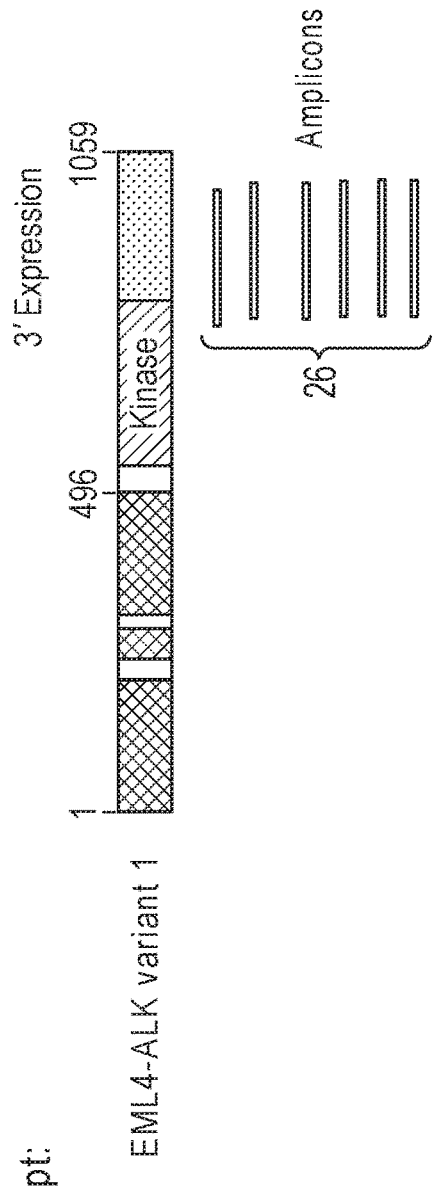
FIG. 2A
FIG. 2B

| # | Exon Tiling Fusion imbalance (breakpoint, p-value, imbalance score) | Targeted Fusions (all passed QC) | Read Counts | Mol. Counts |
|---|---|---|---|---|
| 1 | ALK (exons15-20, p-val=7.0E-04; imb.=5.3) | KIF5B-ALK.K17A20.COSF1257 | 139 | 8 |
| 2 | ALK (exons15-20, p-val=7.0E-04; imb.=5.3) | EML4-ALK.E13A20.COSF1062.1 | 276 | 12 |
| 3 | ALK (exons15-20, p-val=2.7E-03; imb.=5.23) | EML4-ALK.E20A20.COSF409.2 | 207 | 11 |
| 4 | ALK (exons15-20, p-val=2.0E-03; imb.=5.3) | EML4-ALK.E13A20.COSF1062.1 | 139 | 8 |
| 5 | ALK (exons15-20, p-val=7.0E-04; imb.=5.17) | HIP1-ALK.H21A20 | 364 | 18 |
| 6 | ALK (exons15-20, p-val=6.6E-03; imb.=3.08) | EML4-ALK.E6bA20.AB374362.1 | 71 | 2 |
| 7 | ALK (exons15-20, p-val=7.0E-04; imb.=5.3) | EML4-ALK.E6aA20.AB374361.1 | 673 | 27 |
| 8 | ALK (exons15-20, p-val=7.0E-04; imb.=5.25) | EML4-ALK.E13A20.COSF1062.1 | 711 | 19 |
| 9 | ALK (exons15-20, p-val=7.0E-04; imb.=5.29) | EML4-ALK.E13A20.COSF1062.1 | 694 | 23 |
| 10 | ALK (exons15-20, p-val=7.0E-04; imb.=5.3) | EML4-ALK.E13A20.COSF1062.1 | 494 | 18 |
| 11 | ALK (exons15-20, p-val=7.0E-04; imb.=5.3) | KIF5B-ALK.K17A20.COSF1257 | 620 | 36 |

FIG. 20

METHODS FOR PARTNER AGNOSTIC GENE FUSION DETECTION

CROSS-REFERENCE

This application claims the benefit under 35 U.S.C. § 119(e) of U.S. Provisional Application No. 62/822,429, filed Mar. 22, 2019. The entire content of the aforementioned application is incorporated by reference herein.

FIELD

This application generally relates to methods, systems, and computer-readable media for detection of gene fusions, and more specifically, to partner agnostic detection of gene fusions based on targeted RNA sequencing of exon-exon junctions in driver genes using next-generation sequencing technology.

SUMMARY

Gene fusion transcripts resulting from chromosomal rearrangement events in driver genes like ALK, RET, NTRK1 etc. have emerged as crucial biomarkers for cancer diagnosis and for selection of targeted therapies. According to various exemplary embodiments, there are provided methods for detection of gene fusions based on targeted RNA sequencing of some or all of the exon-exon junctions in a driver gene. Measuring the expression of each exon-exon junction and detecting an expression imbalance pattern can predict a gene fusion event in the sample involving that driver gene. The gene fusion events may be detected in a partner agnostic manner, i.e. without using any prior knowledge of the specific fusion partner genes or specific breakpoint information. The methods can detect a fusion involving any of the targeted driver genes in a test sample and can predict an approximate breakpoint location within the driver gene identified as positive for fusions. The gene fusion events are detected and reported along with a confidence score and a p-value. A RNA baseline constructed based on read data from a set of normal samples, improves the robustness and accuracy of the fusion detection. The results of methods described herein can be reported along with results of other methods of fusion detection, such as targeted fusion isoform sequencing.

Detecting gene fusions based on expression imbalance is challenging due to various factors like variability in the RNA expression of driver gene based on sample type, tissue type, barcode multiplexing, and tumor content. The methods described herein address some of these challenges by modeling imbalanced expression signatures in gene-fusion products as a coverage pattern detection problem by placing multiple amplicons per gene in a specific pattern, normalizing the coverage expression values of the amplicons in the driver gene, applying a gene-specific correction with a baseline computed from a set of normal samples, and computing an imbalance score and p-value.

According to an exemplary embodiment, there is provided a method for detecting a gene fusion, comprising (a) amplifying a nucleic acid sample in a presence of a primer pool to produce a plurality of amplicons, the primer pool including primers targeting a plurality of exon-exon junctions of a driver gene, wherein the amplicons correspond to the targeted exon-exon junctions; (b) sequencing the amplicons to generate a plurality of reads; (c) aligning the reads to a reference sequence, the reference sequence including nucleic acid sequences of the amplicons corresponding to the targeted exon-exon junctions of the driver gene; (d) determining a number of reads for each amplicon corresponding to each targeted exon-exon junction; (e) dividing the number of reads for each amplicon by a maximum number of reads among the amplicons of the driver gene to give a normalized read count for each amplicon; (f) applying a baseline correction to the normalized read counts for the amplicons to form corrected read counts, wherein the baseline correction uses baseline values based on read counts for amplicons of a plurality of normal samples; (g) determining an imbalance between the corrected read counts for the amplicons corresponding to a 5' end of the driver gene and the corrected read counts for the amplicons corresponding to a 3'end of the driver gene; and (h) detecting the gene fusion in the driver gene based on the imbalance.

According to an exemplary embodiment, there is provided a system for detecting a gene fusion, comprising a machine-readable memory and a processor in communication with the memory, wherein the processor is configured to execute machine-readable instructions, which, when executed by the processor, cause the system to perform a method comprising (a) receiving, at the processor, a plurality of nucleic acid sequence reads for a plurality of amplicons produced by amplification of a nucleic acid sample a presence of a primer pool, the primer pool including primers targeting a plurality of exon-exon junctions of a driver gene, wherein the amplicons correspond to the exon-exon junctions; (b) aligning the reads to a reference sequence, the reference sequence including nucleic acid sequences of the amplicons corresponding to the targeted exon-exon junctions of the driver gene; (c) determining a number of reads for each amplicon corresponding to each targeted exon-exon junction; (d) dividing the number of reads for each amplicon by a maximum number of reads among the amplicons of the driver gene to give a normalized read count for each amplicon; (e) applying a baseline correction to the normalized read counts for the amplicons to form corrected read counts, wherein the baseline correction uses baseline values based on read counts for amplicons of a plurality of normal samples; (f) determining an imbalance between the corrected read counts for the amplicons corresponding to a 5' end of the driver gene and the corrected read counts for the amplicons corresponding to a 3'end of the driver gene; and (f) detecting the gene fusion in the driver gene based on the imbalance.

According to an exemplary embodiment, there is provided a non-transitory machine-readable storage medium comprising instructions which, when executed by a processor, cause the processor to perform a method for detecting a gene fusion, comprising (a) receiving, at the processor, a plurality of nucleic acid sequence reads for a plurality of amplicons produced by amplification of a nucleic acid sample a presence of a primer pool, the primer pool including primers targeting a plurality of exon-exon junctions of a driver gene, wherein the amplicons correspond to the exon-exon junctions; (b) aligning the reads to a reference sequence, the reference sequence including nucleic acid sequences of the amplicons corresponding to the targeted exon-exon junctions of the driver gene; (c) determining a number of reads for each amplicon corresponding to each targeted exon-exon junction; (d) dividing the number of reads for each amplicon by a maximum number of reads among the amplicons of the driver gene to give a normalized read count for each amplicon; (e) applying a baseline correction to the normalized read counts for the amplicons to form corrected read counts, wherein the baseline correction uses baseline values based on read counts for amplicons of a plurality of normal samples; (f) determining an imbalance between the corrected read counts for the amplicons corresponding to a 5' end of the driver gene and the corrected read counts for the amplicons corresponding to a 3'end of the driver gene; and (f) detecting the gene fusion in the driver gene based on the imbalance.

According to an exemplary embodiment, there is provided a method for detecting a gene fusion, comprising (a) amplifying a nucleic acid sample in a presence of a primer pool to produce a plurality of amplicons, the primer pool including primers targeting a plurality of exon-exon junctions of a driver gene, wherein the amplicons correspond to the exon-exon junctions; (b) sequencing the amplicons to generate a plurality of reads; (c) aligning the reads to a reference sequence; (d) normalizing a number of reads corresponding to each amplicon by dividing the number of reads by a maximum number of reads among the amplicons of the driver gene to give a normalized read count for each amplicon; (e) applying a baseline correction to the normalized read counts for the amplicons of the driver gene to form corrected read counts, wherein the corrected read count for the amplicon is determined by a log 2 of the normalized read count divided by a baseline value for the amplicon; (f) calculating a binary segmentation score for each corrected read count to provide a plurality of binary segmentation scores corresponding to the plurality of amplicons; and (g) determining a predicted breakpoint for the gene fusion based on an amplicon index corresponding to a maximum absolute binary segmentation score.

According to an exemplary embodiment, there is provided a system for detecting a gene fusion, comprising a machine-readable memory and a processor in communication with the memory, wherein the processor is configured to execute machine-readable instructions, which, when executed by the processor, cause the system to perform a method comprising (a) amplifying a nucleic acid sample in a presence of a primer pool to produce a plurality of amplicons, the primer pool including primers targeting a plurality of exon-exon junctions of a driver gene, wherein the amplicons correspond to the exon-exon junctions; (b) sequencing the amplicons to generate a plurality of reads; (c) aligning the reads to a reference sequence; (d) normalizing a number of reads corresponding to each amplicon by dividing the number of reads by a maximum number of reads among the amplicons of the driver gene to give a normalized read count for each amplicon; (e) applying a baseline correction to the normalized read counts for the amplicons of the driver gene to form corrected read counts, wherein the corrected read count for the amplicon is determined by a log 2 of the normalized read count divided by a baseline value for the amplicon; (f) calculating a binary segmentation score for each corrected read count to provide a plurality of binary segmentation scores corresponding to the plurality of amplicons; and (g) determining a predicted breakpoint for the gene fusion based on an amplicon index corresponding to a maximum absolute binary segmentation score.

According to an exemplary embodiment, there is provided a non-transitory machine-readable storage medium comprising instructions which, when executed by a processor, cause the processor to perform a method for detecting a gene fusion, comprising (a) amplifying a nucleic acid sample in a presence of a primer pool to produce a plurality of amplicons, the primer pool including primers targeting a plurality of exon-exon junctions of a driver gene, wherein the amplicons correspond to the exon-exon junctions; (b) sequencing the amplicons to generate a plurality of reads; (c) aligning the reads to a reference sequence; (d) normalizing a number of reads corresponding to each amplicon by dividing the number of reads by a maximum number of reads among the amplicons of the driver gene to give a normalized read count for each amplicon; (e) applying a baseline correction to the normalized read counts for the amplicons of the driver gene to form corrected read counts, wherein the corrected read count for the amplicon is determined by a log 2 of the normalized read count divided by a baseline value for the amplicon; (f) calculating a binary segmentation score for each corrected read count to provide a plurality of binary segmentation scores corresponding to the plurality of amplicons; and (g) determining a predicted breakpoint for the gene fusion based on an amplicon index corresponding to a maximum absolute binary segmentation score.

BRIEF DESCRIPTION OF THE DRAWINGS

The novel features of the invention are set forth with particularity in the appended claims. A better understanding of the features and advantages will be obtained by reference to the following detailed description that sets forth illustrative embodiments and the accompanying drawings of which:

FIG. 2A illustrates an example of approximately balanced 3'/5' expression coverage pattern in a fusion negative sample.

FIG. 2B illustrates an example of significantly imbalanced 3'/5' expression coverage pattern in fusion positive sample.

FIG. 20 gives a table of examples of results for exon tiling fusion imbalance and targeted fusion for FFPE samples that are known positives for fusions in ALK.

DETAILED DESCRIPTION

Figure 1:
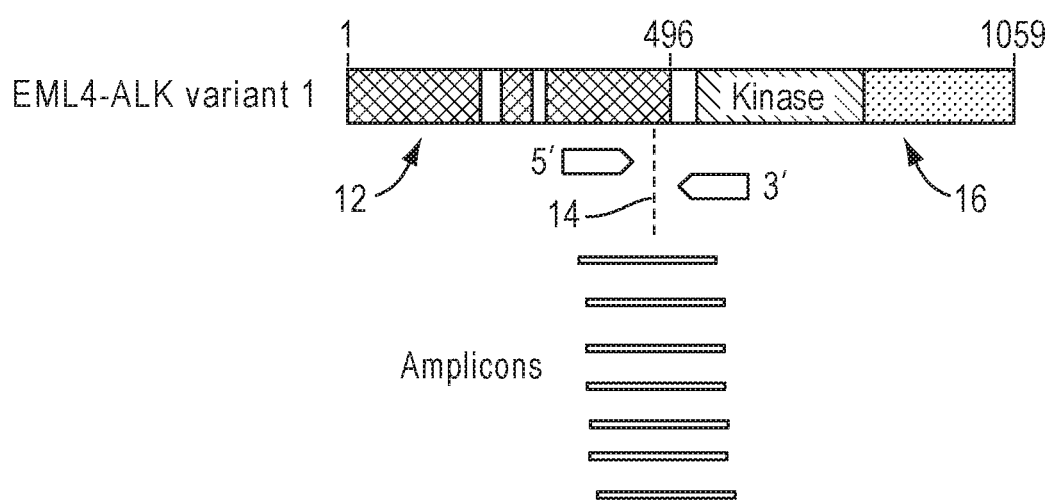
FIG. 1 illustrates an example of a primer design and amplicons targeting an EML4-ALK fusion.

In accordance with the teachings and principles embodied in this application, new methods, systems and non-transitory machine-readable storage medium are provided for partner agnostic detection of gene fusions based on targeted RNA sequencing of exon-exon junctions in driver genes and imbalance between 5' expression and 3' expression.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read," or "nucleic acid sequence read," or "sequence read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The term "locus" as used herein refers to a specific position on a chromosome or a nucleic acid molecule. Alleles of a locus are located at identical sites on homologous chromosomes.

As used herein, the terms "adapter" or "adapter and its complements" and their derivatives, refers to any linear oligonucleotide which can be ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

As used herein, "DNA barcode" or "DNA tagging sequence" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode or DNA tagging sequence can be incorporated into the nucleotide sequence of an adapter.

In some embodiments, the disclosure provides for amplification of multiple target-specific sequences from a population of target nucleic acid molecules. In some embodiments, the method comprises hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the digesting includes partial digesting of one or more of the target-specific primers from the amplified target sequence. In some embodiments, the amplified target sequences can be ligated to one or more adapters. In some embodiments, adapters can include one or more DNA barcodes or tagging sequences. In some embodiments, amplified target sequences once ligated to an adapter can undergo a nick translation reaction and/or further amplification to generate a library of adapter-ligated amplified target sequences.

In some embodiments, the methods of the disclosure include selectively amplifying target sequences in a sample containing a plurality of nucleic acid molecules and ligating the amplified target sequences to at least one adapter and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

A plurality of defined spaces or reaction confinement regions may be arranged in an array, and each defined space or reaction confinement regions may be in electrical communication with at least one sensor to allow detection or measurement of one or more detectable or measurable parameter or characteristics. This array is referred to herein as a sensor array. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal.

In various embodiments, the phrase "base space" refers to a representation of the sequence of nucleotides. The phrase "flow space" refers to a representation of the incorporation event or non-incorporation event for a particular nucleotide flow. For example, flow space can be a series of values representing a nucleotide incorporation event (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event; however, any other symbol or designation could be used alternatively to represent and/or identify these events and non-events. In particular, when multiple nucleotides are incorporated at a given position, such as for a homopolymer stretch, the value can be proportional to the number of nucleotide incorporation events and thus the length of the homopolymer stretch.

FIG. 1 illustrates an example of a primer pair design and amplicons targeting an EML4-ALK fusion. For targeted fusion isoforms, primer design is limited to known fusion products (i.e., chimeric gene fusions between driver genes and partner genes) at known fusion breakpoints. In this example, the EML4 portion 12 and ALK portion 16 are fused at breakpoint 14. The resulting amplicons align across the breakpoint 14, with a portion of each amplicon on either side. Common variations in the population require multiple isoforms to support the variations of breakpoint locations. Driver genes could partner with dozens of genes in many breakpoints.

FIGS. 2A and 2B illustrate an example of detecting fusions with 3'/5' expression coverage imbalance. In this example, ALK is the driver gene. In a wild type transcript of the driver gene as shown in FIG. 2A, amplicons 22 for the 5' and amplicons 24 for the 3' have approximately balanced expression patterns in fusion negative samples. In samples positive for fusion involving the driver gene as shown in FIG. 2B, there will be a significant imbalance between 5' expression and 3' expression 26 of the driver gene in favor of increased expression in the latter, owing to enhanced expression of the fusion transcript. For fusion positive samples, only the fusion transcript or both the fusion and wild type transcripts is/are expressed.

Figure 3:
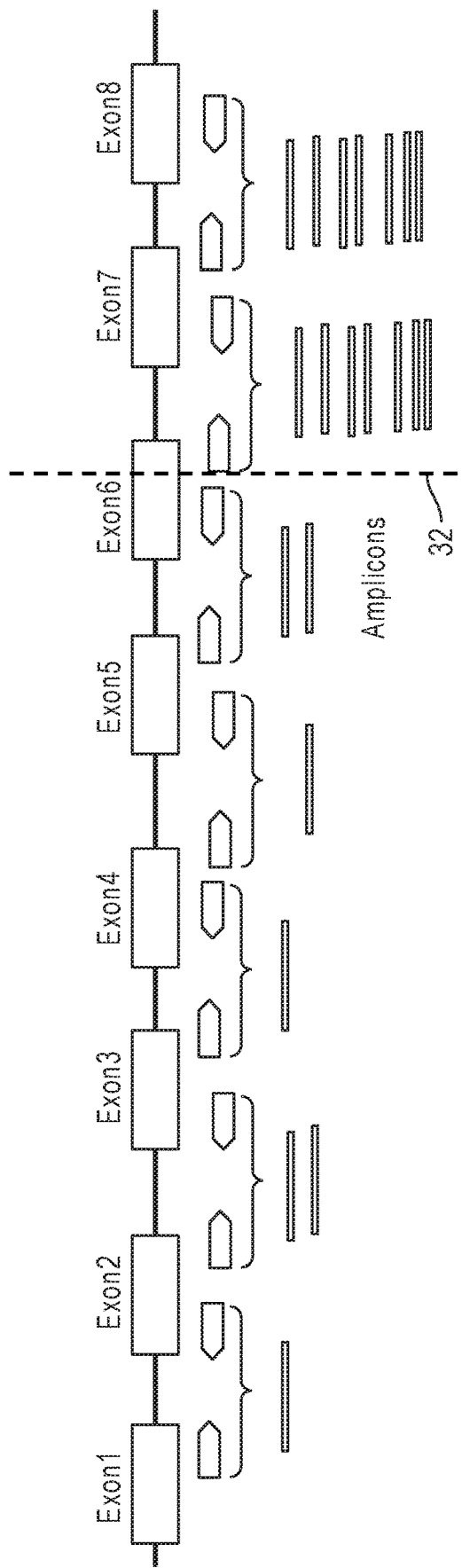
FIG. 3 illustrates an example of an exon tiling coverage analysis for detecting fusions.

FIG. 3 illustrates an example of an exon tiling coverage analysis for detecting fusions. For this example, one amplicon is designed per exon-exon junction of the driver gene. The amplicon coverage pattern shows an increase in counts after the exon-exon junction for exon 6 and exon 7, indicating the presence of a breakpoint 32.

Figure 4A:
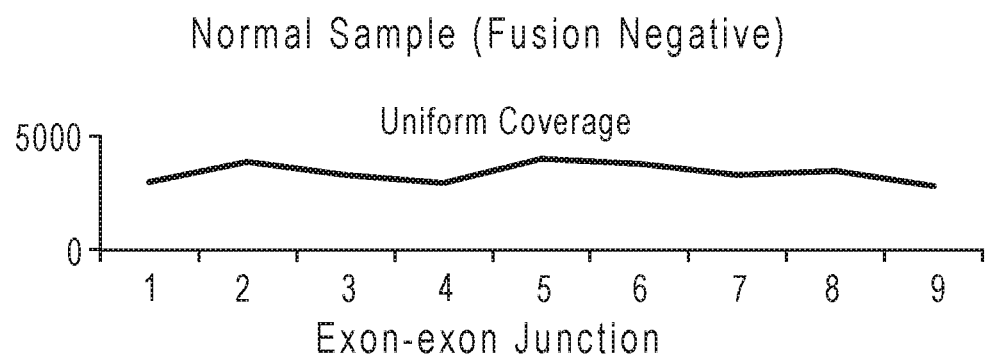
FIG. 4A shows an example of wild-type transcript coverage pattern in the driver gene amplicons in a normal sample.
Figure 4B:
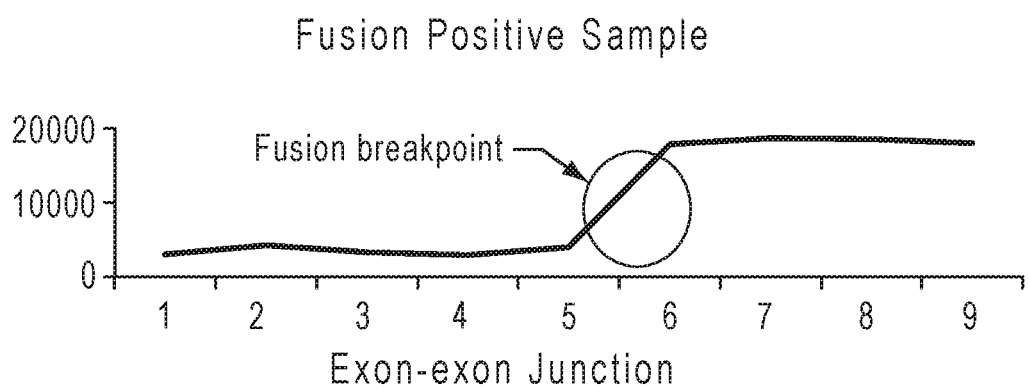
FIG. 4B shows an example of transcript coverage pattern in the driver gene amplicons for a fusion positive sample.

FIGS. 4A and 4B show schematic examples of coverage patterns across the gene for wild type transcript in a normal sample (FIG. 4A) and in a fusion positive sample (FIG. 4B). The y-axis represents read counts after normalizing with respect to a baseline. The x-axis represents intron indices corresponding to the exon-exon junctions. FIG. 4A shows a fairly uniform read coverage across the gene for the normal sample. FIG. 4B shows a sharp increase in coverage after the breakpoint the fusion positive sample.

In some embodiments, design guidelines for primers for amplicons for use in exon tiling fusion detection include one or more of the following:
  Uniform amplicon length in the preferred range of 90-100 bp
  Uniform GC Content in the preferred range of 40-60%
  Placement of amplicons around the known fusion breakpoint in each gene
    At least 3 amplicons on each side of the known breakpoint
  Do not span the exon-exon junction of the most common breakpoint
    This avoids sharing of the primer for the most common fusion (e.g.: ALK Exon 20)
  Priority of driver genes for partner agnostic fusion detection
  RNA expression levels of genes across several tissue types
  Minimize conflicts with the other RNA targeted fusion primers In some embodiments, the design targets fusion breakpoints occurring in close proximity to untranslated regions (UTR) of a gene (e.g., in driver genes FGFR2 and FGFR3, that more frequently fuse at the 5' end, with fusion junction occurring towards their 3pUTR). In those cases, exon-exon junction amplicons may be supplemented with additional designs at the UTR regions, so that sufficient sampling of the expression of both sides of the breakpoint is retained.

In some embodiments, the amplicon tiling of the exon-exon junctions of the driver gene may be separated from exons of a known breakpoint area. Primers designed to generate amplicons for a targeted isoform of a known fusion product may be used in addition to the primers for amplicon tiling. The targeted isoform for the known breakpoint may be tested in addition to the detection of possible de novo breakpoints elsewhere in the gene using the tiling amplicons. In some embodiments, when testing for a possible breakpoint near the edge of the driver gene, the amplicon tiling may span the boundary of the exon on the edge with an untranslated region (UTR).

In some embodiments, Table 1 gives an example of exon tiling assays.

TABLE 1

| Type | Gene | Transcript ID | #Amplicons |
|---|---|---|---|
| Driver Gene | NTRK1 | ENST00000524377 | 7 |
| | NTRK2 | ENST00000376214 | 11 |
| | NTRK3 | ENST00000394480 | 13 |
| | RET | ENST00000340058 | 10 |
| | ALK | ENST00000389048 | 14 |
| | ROS1 | ENST00000368508 | 16 |
| | BRAF | ENST00000288602 | 10 |
| | NRG1 | ENST00000287842 | 6 |
| | FGFR1 | ENST00000447712 | 10 |
| | FGFR2 | ENST00000358487 | 9 |
| | FGFR3 | ENST00000440486 | 8 |
| | ESR1 | ENST00000440973 | 9 |
| | MET | ENST00000397752 | 8 |
| | NUTM1 | ENST00000438749 | 6 |
| Control gene | HMBS | ENST00000537841 | 8 |
| | ITGB7 | ENST00000267082 | 9 |

In some embodiments, fewer genes may be included, such as in the example of Table 2.

TABLE 2

| Type | Gene | Transcript ID | #Amplicons |
|---|---|---|---|
| Driver Gene | NTRK1 | ENST00000524377 | 7 |
| | NTRK2 | ENST00000376214 | 11 |
| | NTRK3 | ENST00000394480 | 13 |
| | RET | ENST00000340058 | 10 |
| | ALK | ENST00000389048 | 14 |
| | FGFR2 | ENST00000358487 | 8 |
| Control gene | HMBS | ENST00000537841 | 8 |
| | ITGB7 | ENST00000267082 | 9 |

In various embodiments, other combinations of genes and numbers of amplicons may be provided for exon tiling assays.

In some embodiments, the 5' primer and 3' primer for a given exon-exon junction each have a molecular tag. For identifying individual polynucleotide molecules, molecular tags are appended to the 5' primer and the 3' primer, respectively, including a prefix tag appended to the 5' primer and a suffix tag appended to the 3' primer. Individual polynucleotide molecules are labeled with unique molecular tags, amplified in a PCR reaction and sequenced generating exon tiling amplicons. The exon tiling amplicons for a given targeted fusion may include the prefix tag for the 5' end and the suffix tag for the 3'end. PCR amplification and sequencing may produce multiple amplicons resulting in multiple sequence reads per original tagged polynucleotide molecule when the corresponding exon-exon junction is present. The unique molecular tag is used to identify the sequence reads that originate from the same polynucleotide molecule and classify them into families having the same tag sequence.

A family, or molecular family, refers the set of sequence reads having the same unique molecular tags. The family size is the number of sequence reads in the family. A functional family is a family that has a number of members that is greater than a minimum family size. The minimum family size can be any integer value. For example, the minimum family size can be three or greater. Molecular counts corresponding to a particular amplicon is the number of families counted for that amplicon.

Figure 5A:
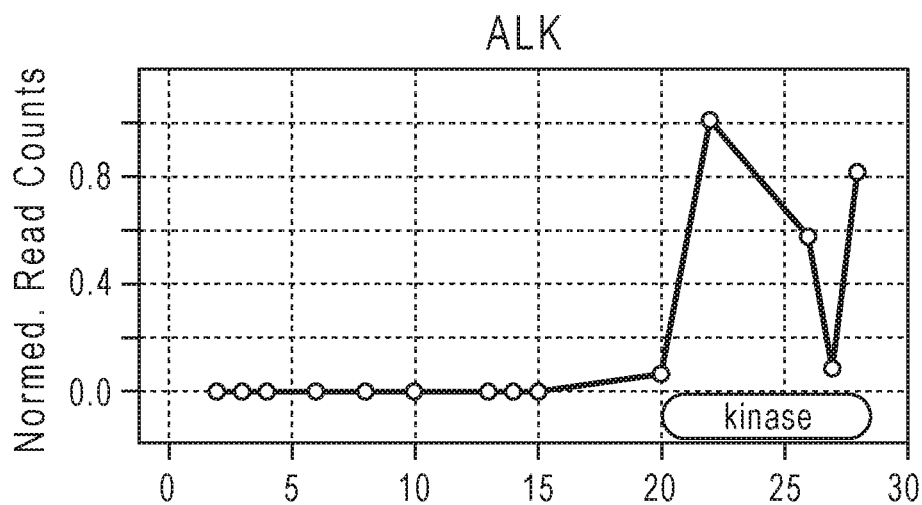
FIG. 5A is an example of a plot of the normalized read counts for targeted exon-exon junctions of the ALK gene.
Figure 5B:
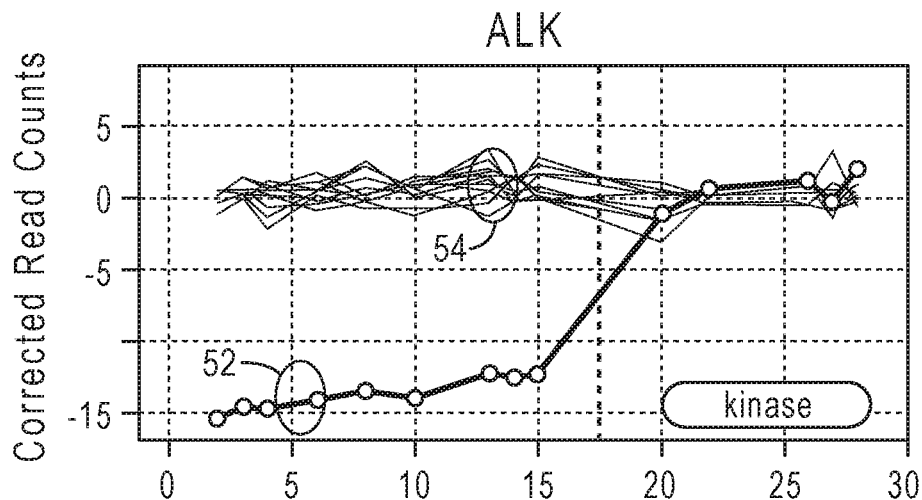
FIG. 5B shows an example of corrected read counts for the targeted exon-exon junctions after baseline correction, as well as plots of normalized and baseline-corrected read counts for a group of normal samples.
Figure 5C:
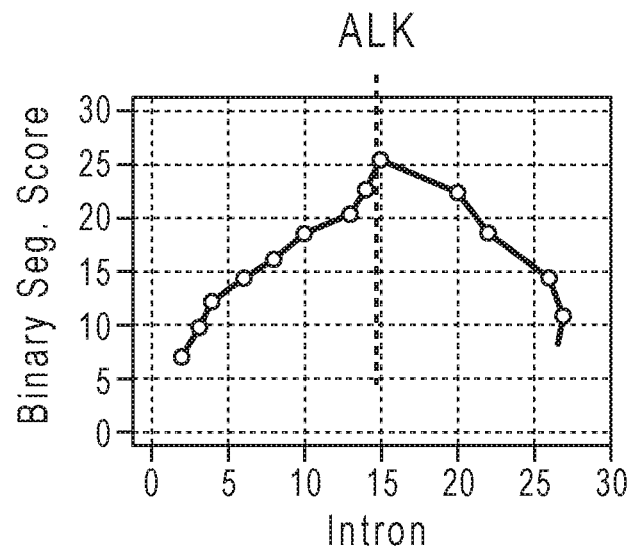
FIG. 5C shows an example of a plot of the binary segmentation scores $Z_i$ (computed from the baseline-corrected profile of FIG. 5B) corresponding to amplicons of the ALK gene.

In FIGS. 5A-5C, the numbers on the x-axis labeled "intron" displayed for the gene correspond to indices for exon-exon junctions of transcript RNA (i.e., the intron indices do not represent physical intron sequences in a DNA strand). The circles on the plots in FIGS. 5A-5C indicate targeted exon-exon junctions that are targeted by primers, such that amplicon coverage data are produced at those locations. The number of locations for the amplicons is less than or equal to the total number of exon-exon junctions in the gene.

FIG. 5A is an example of a plot of normalized read counts for targeted exon-exon junctions in the ALK gene. In FIG. 5A, the amplicon at intron index 26 in the kinase region shows a sharply lower number of normalized reads than those of adjacent amplicons. Possible causes for this drop in amplicon coverage include impaired amplicon primer binding, splicing isoform resulting in exon skipping or other technical biases. The coverages for this amplicon will often be systematically lower in all the samples, including the normal samples. The baseline correction mitigates this problem, as shown by the corrected read counts in FIG. 5B.

In some embodiments, an imbalance analysis is applied to detect fusions based on read counts obtained from exon-tiling amplicons. Input to the imbalance analysis is the number of reads, or coverage, for amplicons corresponding to exon-exon junctions targeted in an exon-tiling of the gene in a test sample. For example, the input information can be provided in a BAM file. A baseline is determined from the number of reads for amplicons of the gene obtained from a number of normal samples that are negative for the gene fusion. The order of the steps is exemplary and different orders of steps are possible in various embodiments.

1) Normalize the number of reads for each amplicon of the gene by dividing the number of reads by the maximum number of reads among the amplicons of the gene to give normalized read counts for each amplicon. FIG. 5A is an example of a plot of the normalized read counts for each targeted exon-exon junction of the ALK gene.

2) Compute a baseline from a set of 40-60 normal samples (i.e., fusion negative samples validated with orthogonal methods) for use in baseline correction. The read counts of the gene amplicons in each normal sample are normalized by dividing the number of reads of each gene amplicon by the number of reads of the gene amplicon with the highest coverage in the normal sample. The baseline value for each amplicon is computed as the median of normalized values for the amplicons across all the normal samples. Alternatively, the mean of normalized read counts for each amplicon of the gene may be calculated to give the baseline values.

3) Apply a baseline correction to the normalized read counts for the amplicons of the gene of the test sample to form corrected read counts. For each amplicon of the gene of the test sample, the corrected read count may be calculated by:

Corrected read count=log$_2$[normalized read count of amplicon in test sample÷baseline value of the amplicon]

FIG. 5B shows an example of plots of corrected read counts 52 for each targeted exon-exon junction after baseline correction, as well as plots of normalized and baseline-corrected read counts for a group of normal samples 54. FIG. 5B shows an example of a plot of the corrected read counts 52 for each exon-exon junction of the ALK gene shown in FIG. 5A.

4) Calculate a binary segmentation score. For amplicon measurements $X_1$ to $X_n$, each $X_i$ represents the corrected read count for the $i^{th}$ amplicon, corresponding to an $i^{th}$ exon-exon junction, where X is a total number of corrected read counts and n is the number of amplicons in the series. For example, in FIG. 5B, each data point of corrected read counts corresponds to an X in a series of amplicon measurements from $X_1$ to $X_n$, where n=14. The binary segmentation score may be calculated as follows:

a. Calculate a partial sum of amplicon measurements from the first to the $i^{th}$ amplicons, $S_i$:

$S_i = X_1 + \ldots + X_i$ b. Calculate a sum of all the amplicon measurements from the first to the $n^{th}$ amplicons, $S_n$, where n is a total number of corrected read counts:

$S_n = X_1 + \ldots + X_n$ c. Calculate the binary segmentation score $Z_i$: (for measurements $X_1 \ldots X_{n-1}$)

$$Z_i = \frac{\frac{S_i}{i} - \frac{S_n - S_i}{n - i}}{\sqrt{\frac{1}{i} + \frac{1}{n-1}}}$$

FIG. 5C shows an example of a plot of the binary segmentation scores $Z_i$ corresponding to amplicons of the ALK gene.

d. Find the amplicon index i corresponding to the maximum absolute binary segmentation score $|Z_i|$. The predicted breakpoint b is the amplicon index $i_{max}$ corresponding to the maximum absolute binary segmentation score $Z_{max}$ for the gene. The physical fusion breakpoint in the gene can be located in the range between the amplicon index $i_{max}$ corresponding to maximum absolute binary segmentation score $Z_{max}$ and the next amplicon index ($i_{max}$+1). For the example of FIG. 5C, a breakpoint region is indicated between intron indices 15 and 20, or after the amplicon index=9 corresponding to the maximum absolute binary segmentation score $Z_{max} = |Z_p|$.

Figure 6:
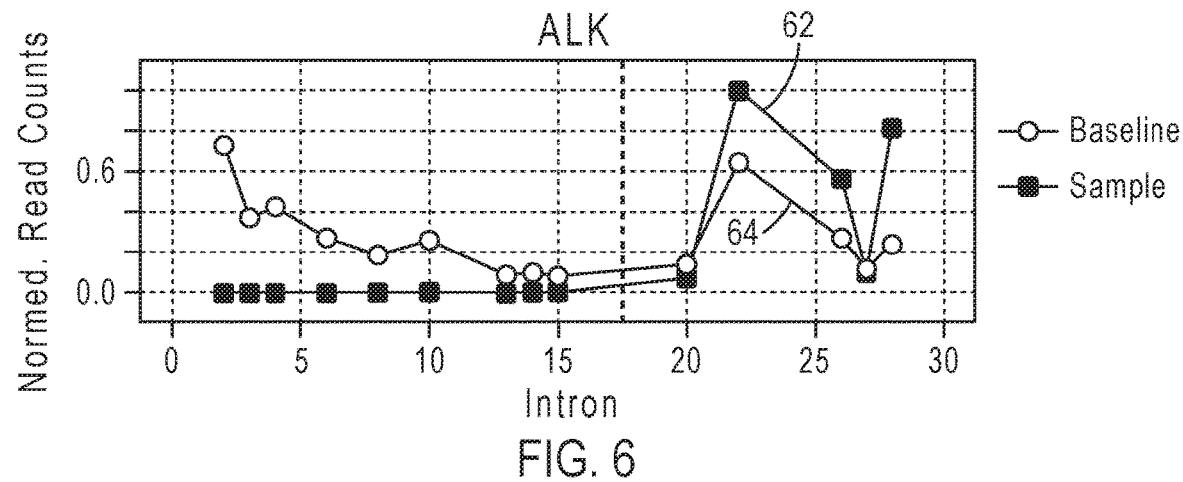
FIG. 6 gives examples of plots of normalized read counts per amplicon and a plot of baseline normalized read counts per amplicon in ALK gene.

5) Calculate the imbalance score. The array U is defined as an array of N amplicons with normalized read counts per amplicon and the array V is defined as an array of N baseline normalized read counts for amplicons from normal samples, where N is the total number of amplicons measured. The array of N baseline normalized read counts includes the baseline value for each amplicon calculated in step 2). FIG. 6 gives examples of a plot of normalized read counts per amplicon 62 and a plot of baseline normalized read counts per amplicon 64. The circles indicate normalized read counts for the measured amplicons. The imbalance score is calculated as follows:

a. Calculate an expected imbalance value based on the baseline normalized read counts (baseline values) in array V. In the partial sum $\{V[(1+b):N])\}$, b is the predicted breakpoint determined by the binary segmentation score of the test sample, and the sum of baseline normalized read counts is calculated from array element (1+b) to array element N.

Expected Imbalance=sum$\{V[(1+b):N])\}$/sum$[V(1:N)]$

This calculation of expected imbalance is used for determining a 3'/5' imbalance score in step 5)c for the scenario Partner Gene—Driver Gene, where the driver gene is located at the 3' end of a fusion.

b. Calculate an observed imbalance value based on the normalized read counts in array U. In the partial sum $\{U[(1+b):N])\}$, b is the predicted breakpoint determined by the binary segmentation score of the test sample, and the sum of normalized read counts is calculated from array element (1+b) to array element N.

Observed Imbalance=sum$\{U[(1+b):N])\}$/sum$[U(1:N)]$

This calculation of observed imbalance is used for determining a 3'/5' imbalance score in step 5)c for the scenario Partner Gene—Driver Gene, where the driver gene is located at the 3' end of a fusion.

c. The imbalance score is the ratio of the observed imbalance value and the expected imbalance value.

Imbalance score=Observed Imbalance/Expected Imbalance d. In cases where a driver gene may fuse at the 5' end, the imbalance calculations of steps 5)a and 5)b are inverted as following:

Expected Imbalance=sum$\{V[1:b])\}$/sum$[V(1:N)]$

Observed Imbalance=sum$\{U[1:b])\}$/sum$[U(1:N)]$

These calculations of expected imbalance and observed imbalance are used for determining a 5'/3' imbalance score in step 5)c for the scenario Driver Gene—Partner Gene, where the driver gene is located at the 5' end of a fusion.

Figure 7A:
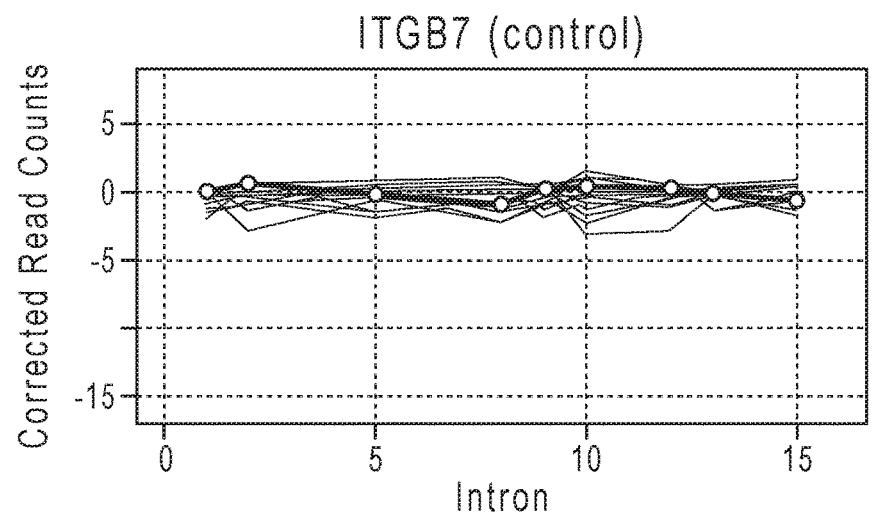
FIG. 7A shows an example of plots of baseline corrected read counts for the control gene ITGB7.
Figure 7B:
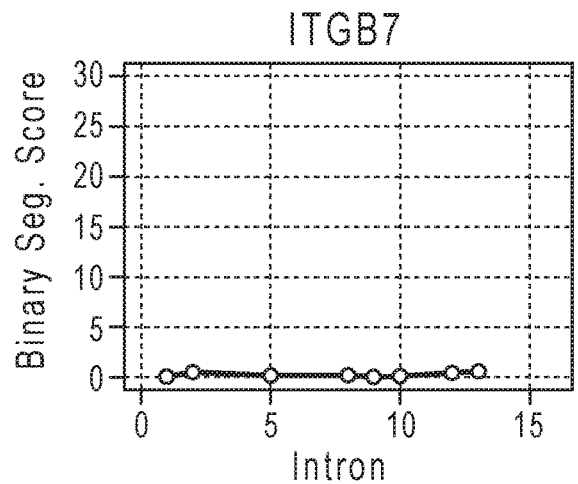
FIG. 7B shows an example of a plot of binary segmentation scores for the control gene ITGB7.
Figure 8A:
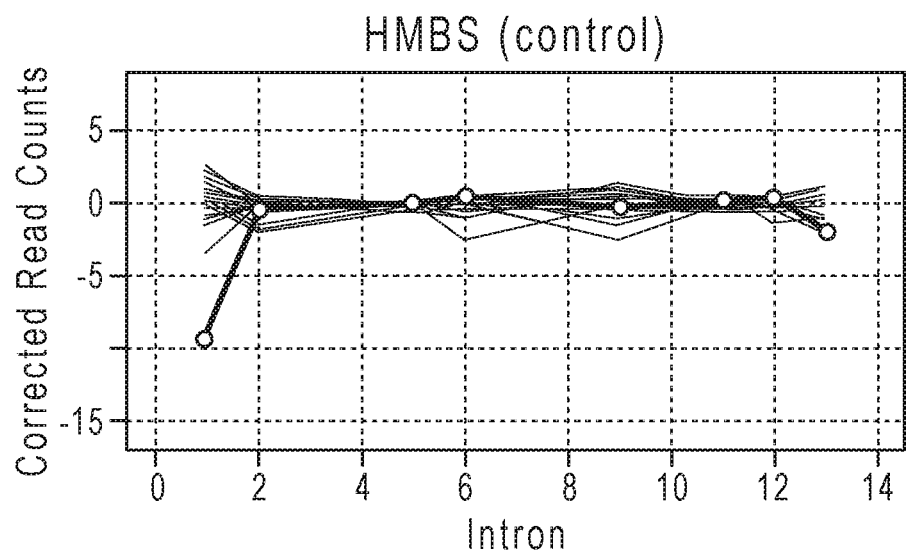
FIG. 8A shows an example of baseline corrected read counts for the control gene HMBS.
Figure 8B:
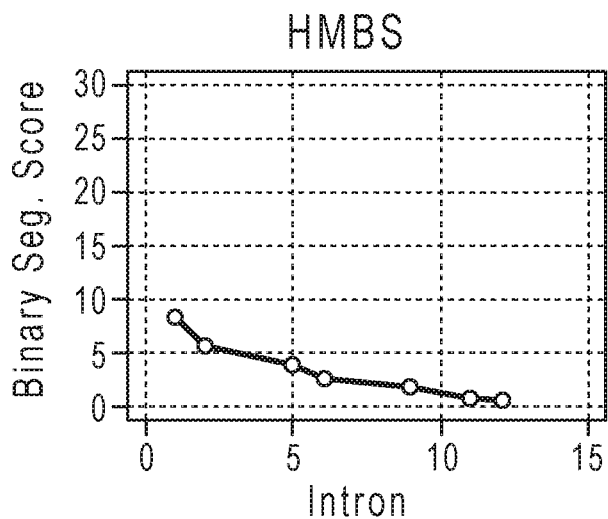
FIG. 8B shows an example of a plot of binary segmentation scores for the control gene HMBS.
Figure 9:
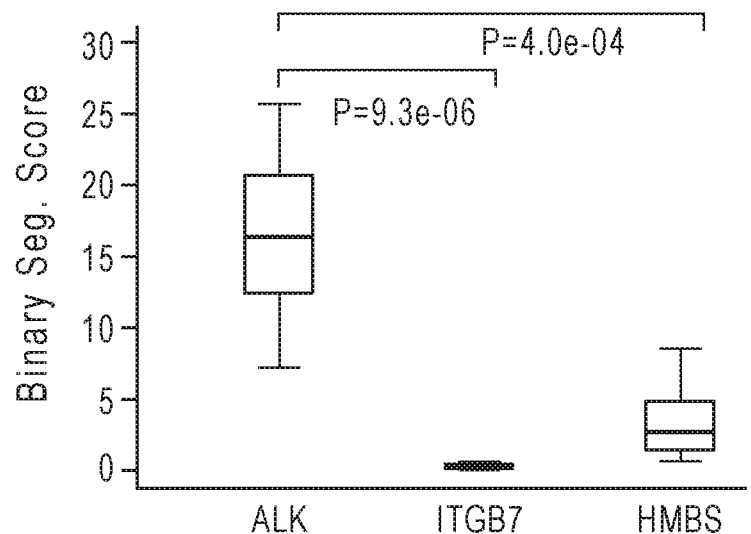
FIG. 9 shows examples of distributions of the binary segmentation scores for the gene ALK of test sample, the ITGB7 control gene and the HMBS control gene.

6) Apply the Wilcoxon rank test to compare the binary segmentation scores of the test sample to binary segmentation scores of the control gene and determine p-values. FIG. 7B shows an example of a plot of binary segmentation scores for the control gene ITGB7 calculated as described in steps 4)a to 4)c. FIG. 7A shows an example of plots of the corrected read counts for each targeted exon-exon junction after baseline correction for ITGB7. FIG. 8B shows an example of a plot of binary segmentation scores for the control gene HMBS calculated as described in steps 4)a to 4)c. FIG. 8A shows an example of plots of the corrected read counts for each targeted exon-exon junction after baseline correction for HMBS. FIG. 9 shows the distributions of the binary segmentation scores for the gene ALK of test sample, the ITGB7 control gene and the HMBS control gene. The p-value is 9.3e-06 with respect to the ITGB7 control gene and 4.0e-04 with respect to the HMBS control gene. For two control genes, the greater of the respective p-values may be used as the p-value for evaluating the significance of the imbalance for fusion detection. In some embodiments, a single control gene may be used for generating a single p-value.

7) Apply thresholds to the imbalance score and the p-value to detect a driver gene fusion. For example, the decision logic may indicate a positive imbalance call when the calculated imbalance score is greater than or equal to the imbalance score threshold for the gene and the calculated p-value is less than or equal to the p-value threshold. Other mathematically equivalent expressions may be used to apply the thresholds. For example, the −log 10(p-value) may be greater than or equal to the −log 10(p-value threshold). The imbalance score threshold and p-value threshold may be gene-specific, as genes markedly differ in their length, common breakpoint positions and their resulting expression imbalance patterns. The expression levels may vary in different genes, so the threshold values may be set for a particular gene. Testing known positive and negative samples from truth sets may be used to set a threshold value for a particular gene. Table 3 gives an example for adjustable gene-specific thresholds for expression imbalance analysis positive calls.

TABLE 3

| Gene | Recommended thresholds | | |
|---|---|---|---|
| | Expression level (average reads from exon-tile amplicons per gene) | Imbalance score | p-value |
| ALK | 50 | 2.5 | 0.05 |
| RET | 100 | 1.5 | 0.05 |
| NTRK1 | 100 | 2.0 | 0.05 |
| NTRK2 | 30 | 3.5 | 0.05 |
| NTRK3 | 30 | 2.5 | 0.05 |

In some embodiments, the read counts for amplicons of the control sample (e.g., ITGB7 or HMBS), are normalized and baseline corrected, as described above in steps 1) to 3).

Background information for the binary segmentation score is described by Olshen, Adam B. et al., "Circular binary segmentation for the analysis of array-based DNA copy number data," *Biostatistics* (2004), Vol. 5 No. 4, pp. 557-572.

In some embodiments, the sequence reads corresponding to exon-tiling amplicons include molecular tags. These sequence reads may be grouped into families sharing common molecular tags. The families may be counted for the amplicons corresponding to the exon-exon junctions to form molecular counts. The imbalance analysis method steps 1) to 7) may be applied to the molecular count, or family count, for each exon-tiling amplicon instead of the read count, or number of reads.

Figure 10:
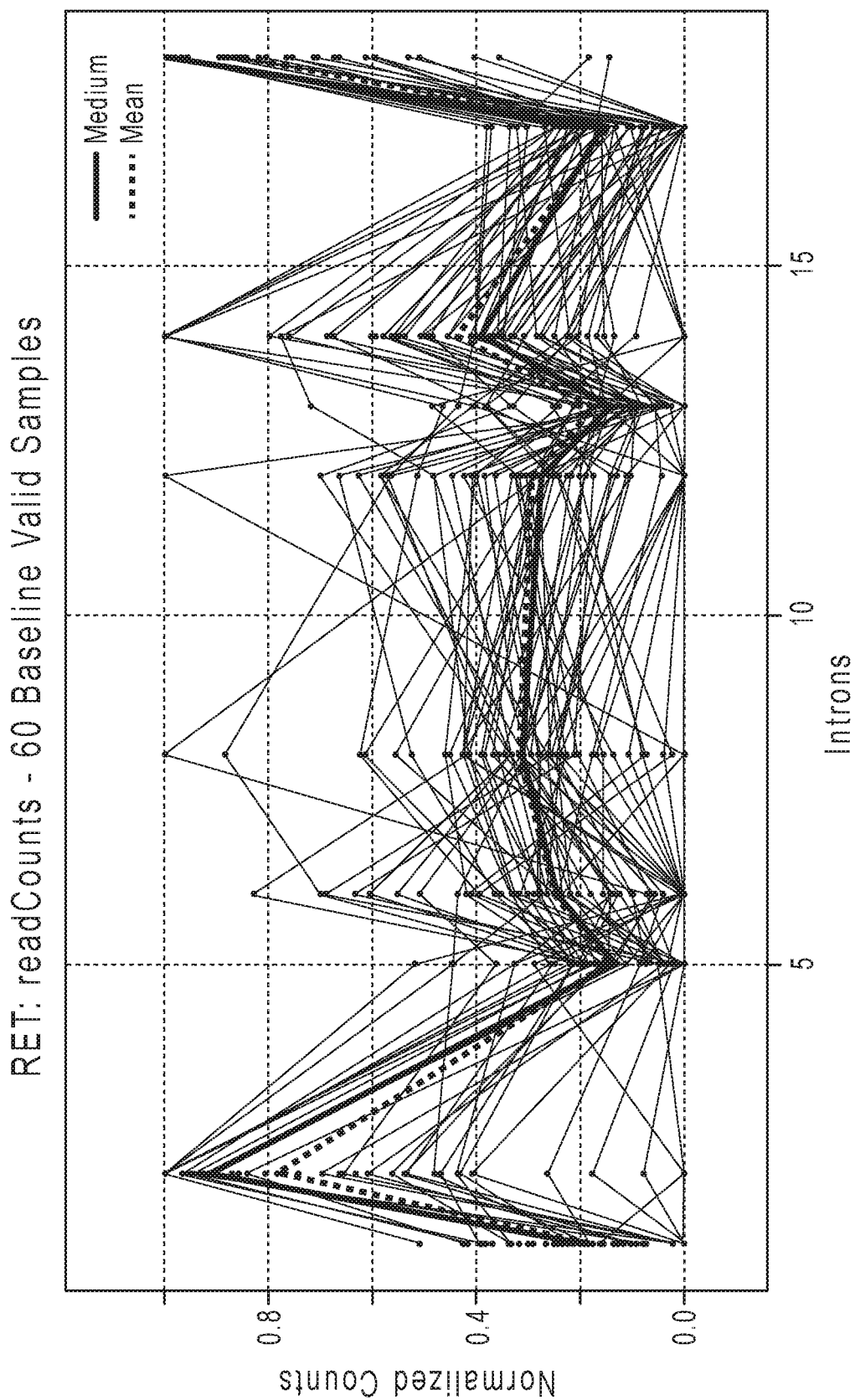
FIG. 10 shows an example of plots of normalized counts from multiple normal samples for determining the baseline for the RET gene.
Figure 11:
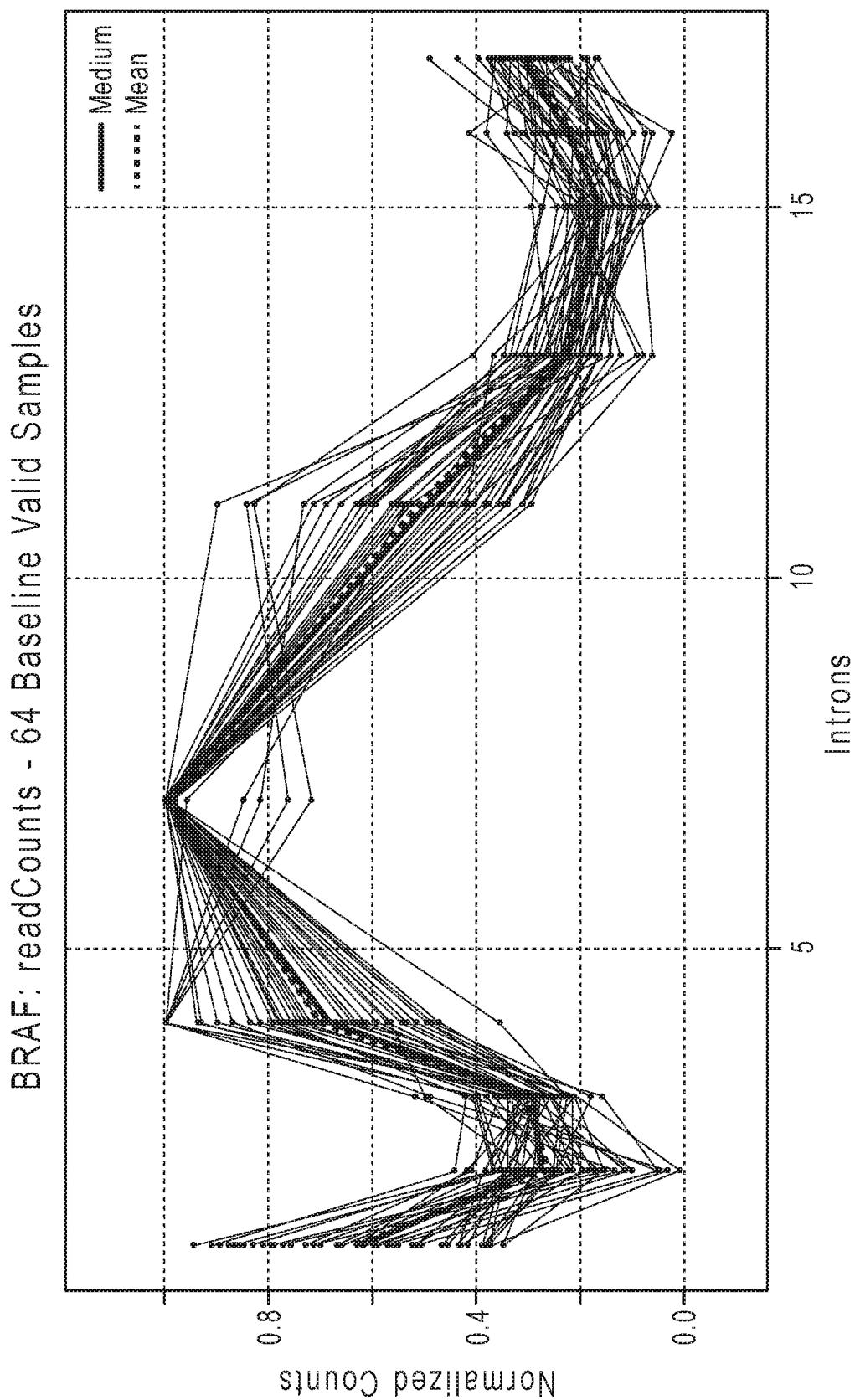
FIG. 11 shows an example of plots of normalized counts from multiple samples for determining the baseline for the BRAF gene.

In some embodiments, the baseline may be determined from read count data collected by testing multiple normal samples from various tissues, such as breast, lung, colon, brain, skin and prostate. For example, the number of samples used to generate measurements for the baseline may be 15 to 64 FFPE samples for each gene baseline, with a median of 59. Larger numbers of normal samples may be used. The read counts for the amplicons of the normal samples may be normalized for the particular gene, as described in step 2) above. Each gene in each sample is normalized with respect to the measured maximum read count for that gene in that sample. The median of normalized read counts for each amplicon of the gene may be calculated to give the baseline. Alternatively, the mean of normalized read counts for each amplicon of the gene may be calculated to give the baseline. A normal sample is included in the baseline calculations for a gene if all of the amplicons have sufficient read counts coverage. For example, normal samples having a median normalized coverage per amplicon of less than 0.1 may be excluded from the baseline. FIGS. 10-11 give examples of normalized counts from multiple normal samples for determining the baseline. The median and mean are also shown. FIG. 10 gives an example of normalized counts from multiple normal samples for determining the baseline for the RET gene. FIG. 11 gives an example of normalized counts from multiple samples for determining the baseline for the BRAF gene.

Figure 12:
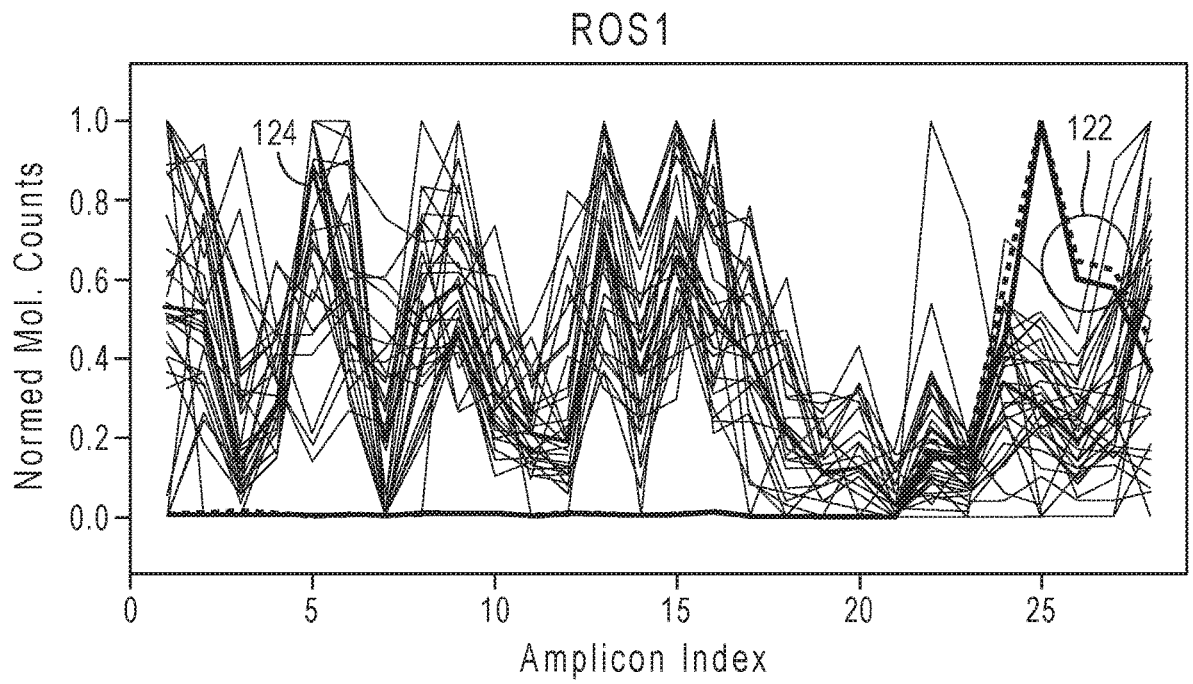
FIG. 12 shows an example of plots of normalized molecular counts of two test samples on a background of normal samples and the baseline computed from them for the ROS1 gene.
Figure 13:
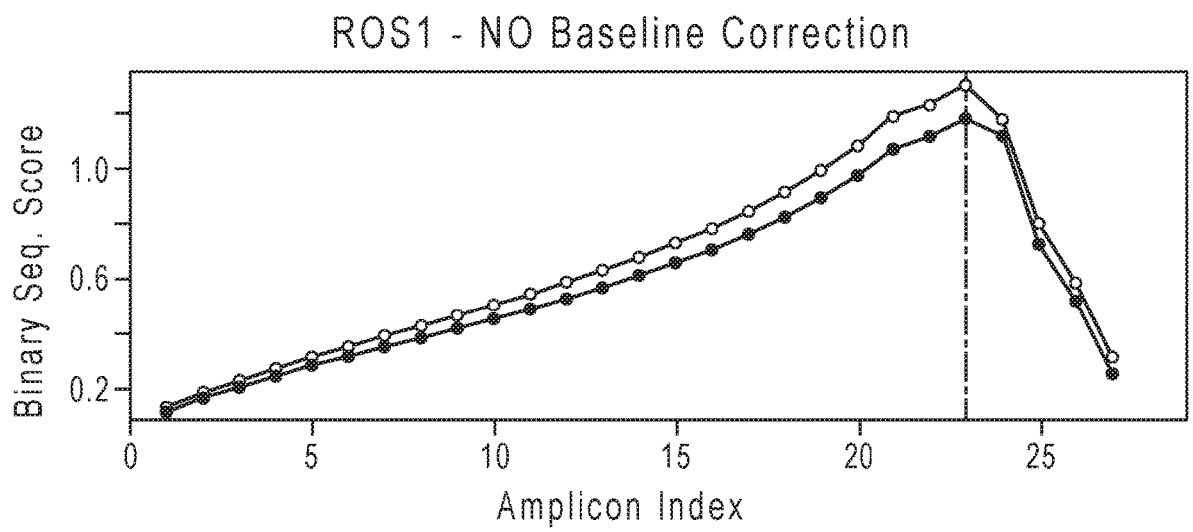
FIG. 13 shows an example of plots of the binary segmentation scores determined for the two ROS1 samples before applying baseline correction.
Figure 14:
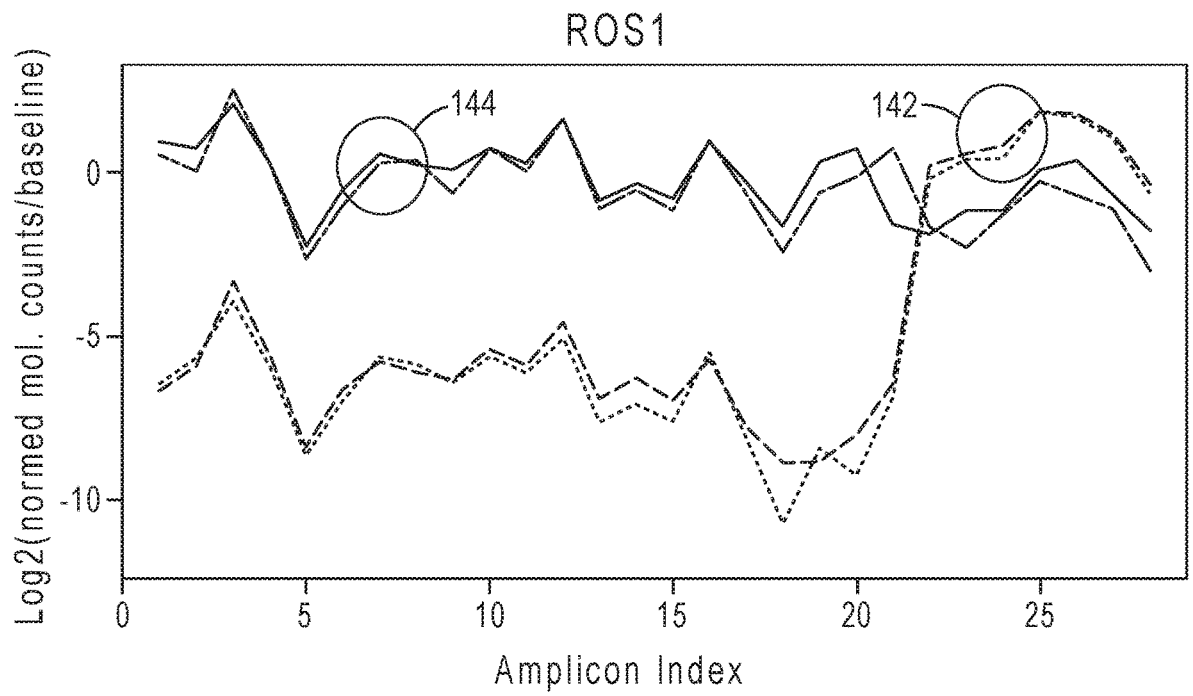
FIG. 14 shows an example of plots of the baseline corrected molecular counts for both a fusion positive sample (2 replicates) 142 and a fusion negative sample (2 replicates) 144.
Figure 15:
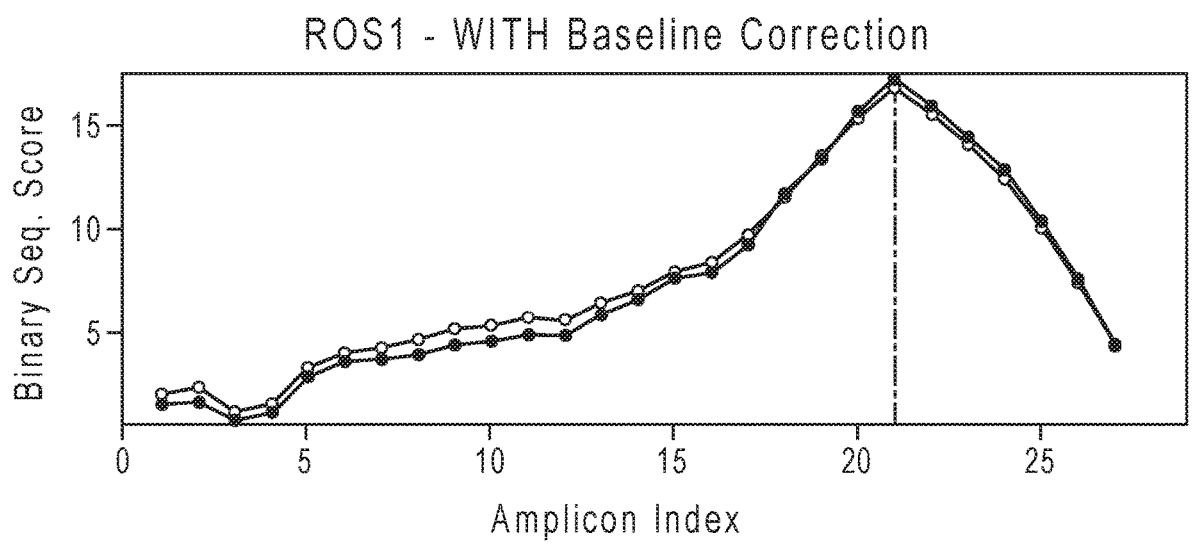
FIG. 15 shows an example of plots of the binary segmentation scores of the fusion positive sample replicates after baseline correction.

Baseline correction can correct for systematic variations in the data, such as GC bias, amplicon specific variations, etc. FIGS. 12 and 13 show examples of results for fusion positive samples for the ROS1 gene before baseline correction. FIG. 12 shows the normalized molecular counts for two replicates of a positive test sample 122 and the baseline 124. FIG. 13 shows the binary segmentation scores determined for the two samples before applying baseline correction. FIG. 13 shows the maximum absolute binary segmentation score at the amplicon index 23 (i.e., the $23^{nd}$ exon-exon junction from the gene 5') corresponding to the predicted breakpoint. FIGS. 14 and 15 show examples of results for two replicates of a fusion positive sample and two replicates of a fusion negative sample for the ROS1 gene after baseline correction. FIG. 14 shows plots of the baseline corrected molecular counts, log 2(normalized molecular counts in test sample/baseline value of the amplicon) for both a fusion positive sample (2 replicates) 142 and a fusion negative sample (2 replicates) 144. FIG. 15 shows the binary segmentation scores of the fusion positive sample replicates after baseline correction. FIG. 15 shows the maximum absolute binary segmentation score at the amplicon index 21 corresponding to the predicted breakpoint. The predicted breakpoint has shifted as a result of the baseline correction, resulting in a more accurate prediction of the breakpoint.

Figure 16:
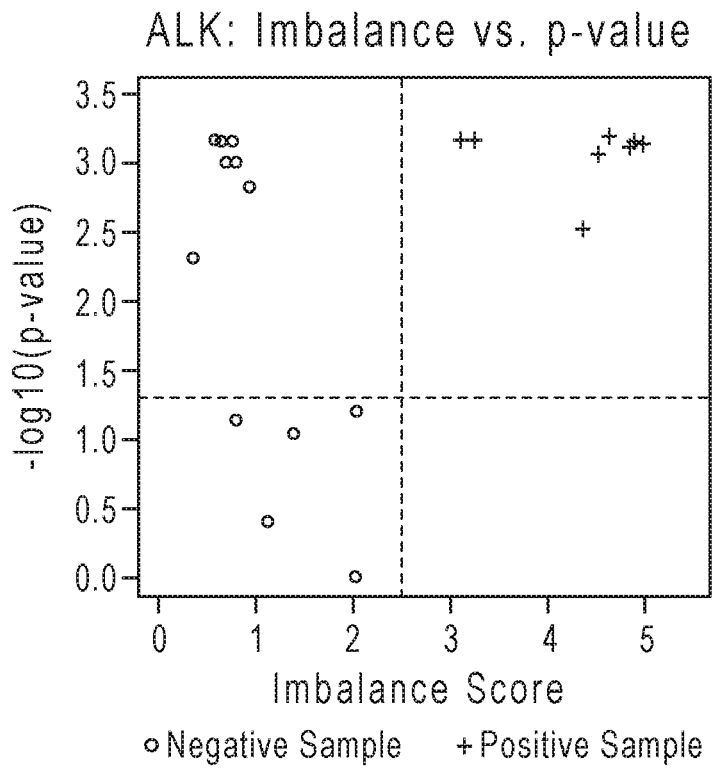
FIG. 16 gives an example of results of fusion detection for the ALK gene.
Figure 17:
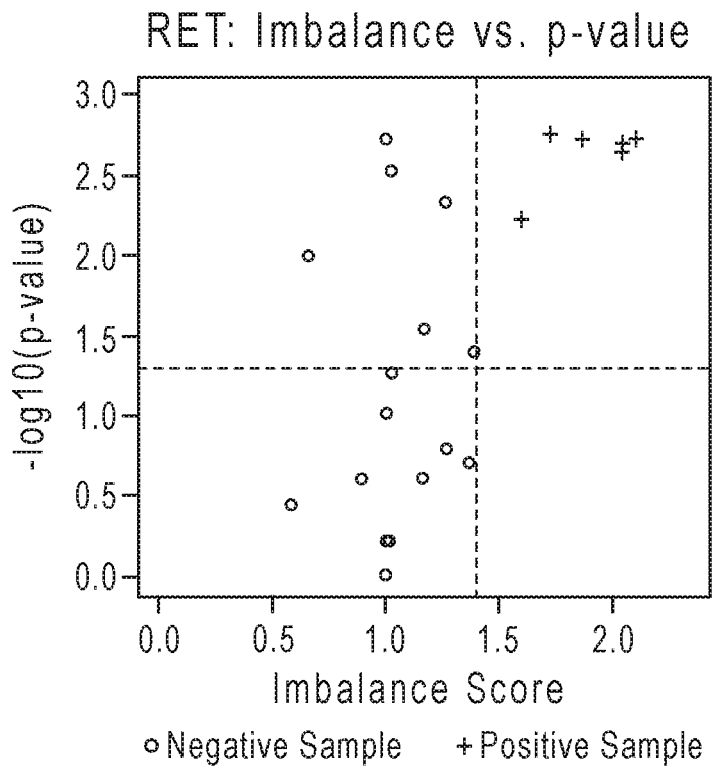
FIG. 17 gives an example of results of fusion detection for the RET gene.
Figure 18:
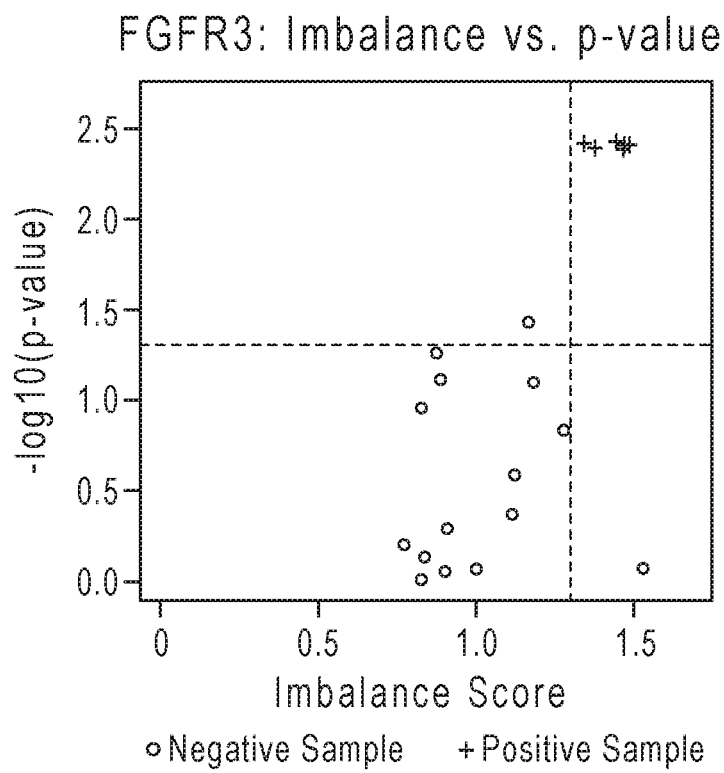
FIG. 18 gives an example of results of fusion detection for the FGFR3 driver gene.
Figure 19:
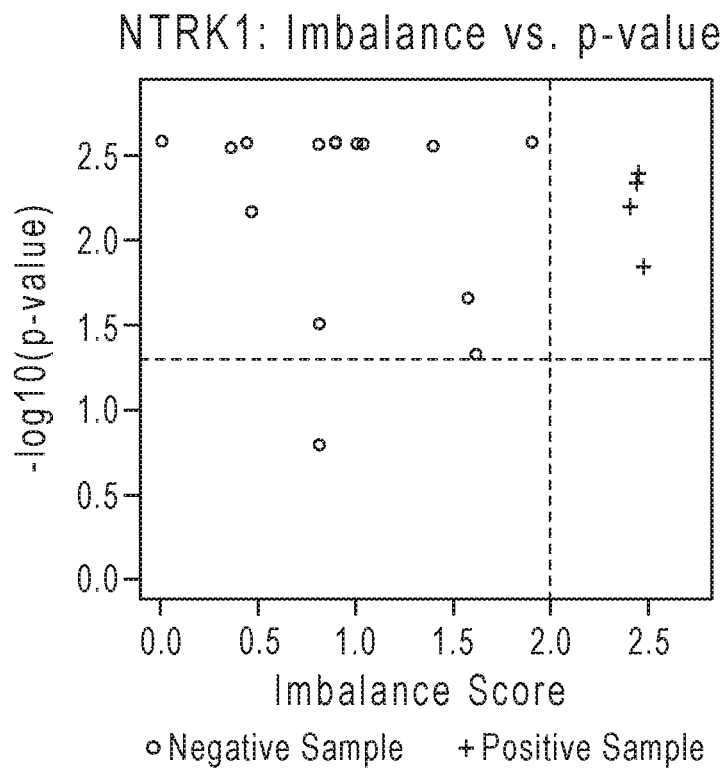
FIG. 19 gives an example of results of fusion detection for the NTRK1 gene.

FIGS. 16-19 give examples of results of fusion detection for different driver genes. These results were generated from testing known positive and negative samples from truth sets for the particular genes. The positive samples were diluted with various backgrounds of a normal sample (fusion negative lung sample) down to concentrations of 2%-20%, exemplifying the Limit of Detection (LOD) range for the assay. FIGS. 16-19 show plots of points representing individual test samples with imbalance score on the x-axis and the negative log 10 of the p-value on the y-axis. Dashed vertical and horizontal lines, representing the designated detection thresholds per-gene, separate the points into quadrants with an upper right positive call quadrant (i.e., imbalance score>imbalance threshold and p-value<p-value threshold). The plus signs represent known fusion positive samples and the circle dots represent known fusion negative FFPE samples. Samples in the upper right had quadrant are called as fusion positive. FIG. 16 gives an example of results for the ALK gene. These results show good classifications of positives (6 samples of ALK fusion cell line diluted to 2% and 2 ALK fusion FFPE clinical research samples diluted to 20%) and negatives for the ALK gene in solid tumor FFPE samples (Formalin Fixed Paraffin Embedded) and cell lines. Similarly, FIG. 17 gives an example of results for the RET gene. These results show overall good classification of fusion positive (5 samples of a RET fusion cell line diluted to 2% and 1 RET FFPE clinical research sample diluted to 20%) and negative samples for the RET gene. FIG. 18 gives an example of results for the FGFR3 driver gene, which more frequently fuses at the 5' end to a partner gene at the 3' end. In this gene, the imbalance scores along the x-axis represent an inverted 5'/3' imbalance measurement, as described above with respect to step 5)d. The plot shows a good classification of positive (6 samples of FGFR3-TACC3 cell line diluted to 20%) and negative FFPE samples. The results show lower imbalance values for the FGFR3 positive values in comparison with other genes, so a lower threshold may be applied to correctly classify the positives while retaining high sensitivity for the assay. FIG. 19 gives an example of results for the NTRK1 gene. Four samples of NTRK1 fusion cell lines were tested. The results show correct classification of the positive samples.

In some embodiments, various thresholds may be applied to call a gene fusion based on imbalance analysis. According to step 7), gene-specific thresholds for the p-value and imbalance score may be applied. For example, the gene-specific thresholds for the p-value may be in the range of 0.05 to 0.1 and the gene-specific threshold for the imbalance score may be in the range of 1.5 to 3.5. In some embodiments additional thresholds may be applied, including mean read counts per amplicon ≥30, mean molecular counts per amplicon ≥3, and the number of amplicons flanking the predicted breakpoint ≥2.

In some embodiments, results of the imbalance call may be combined with results of a targeted isoform call when that information is available. An example of combining the imbalance calls with the targeted isoform calls to give a reported fusion call is given in Table 4.

TABLE 4

| Targeted isoform call | Imbalance call | Fusion call - report |
|---|---|---|
| positive | negative | positive |
| positive | positive | positive |
| negative | negative | negative |
| negative | positive | positive |

FIG. 20 gives a table of examples of results for exon tiling fusion imbalance and targeted fusion for FFPE samples that are known positives for fusions in ALK. The term "exons 15-20" in the second column indicates the predicted range of exon locations for the breakpoint corresponding to the maximum absolute binary segmentation score $Z_{max}$. The exon location of the breakpoint detected for the targeted fusion isoform is indicated by the numbers in the box 2002 in the third column. The predicted ranges of the breakpoints in the second column are consistent with the exon locations of the breakpoints detected by targeted fusion in the box 2002 of column 3. The exon tiling fusion imbalance results for all the sample numbers predicted the correct range for the exon-exon fusion compared to the targeted fusion detection.

Figure 21:
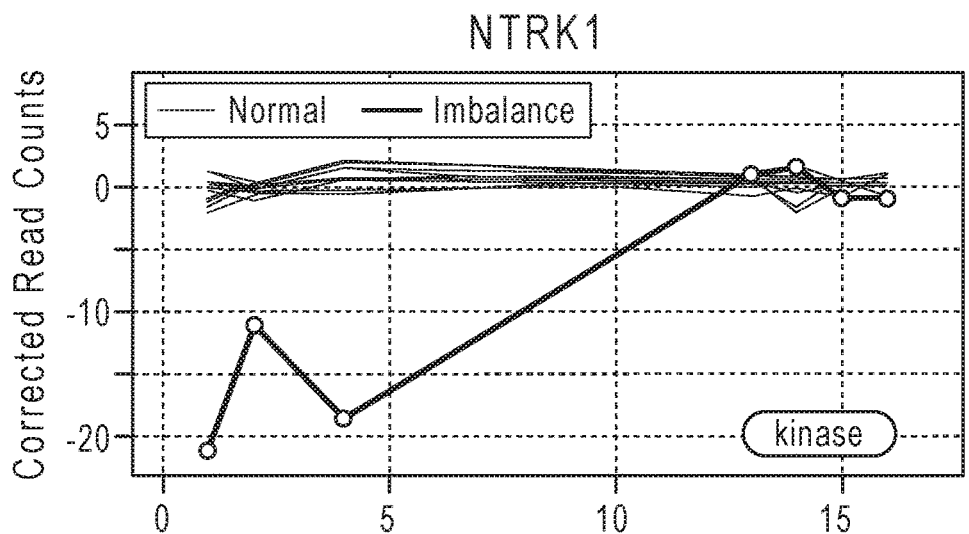
FIG. 21 shows an example of plots of the corrected read counts for the NTRK1 gene.

FIG. 21 shows an example of plots of the corrected read counts for the NTRK1 gene. The NTRK1 clearly shows an imbalance signature with 4 amplicons near the kinase domain expressed at the expected level, and 3 additional amplicons near the 5' end clearly underexpressed. In some embodiments, more amplicons to cover additional exon-exon junctions may reduce the false negatives and improve the fusion imbalance detection. In some embodiments, adjusting the gene-specific thresholds for the imbalance score and/or the p-value may optimize the fusion imbalance detection.

Figure 22:
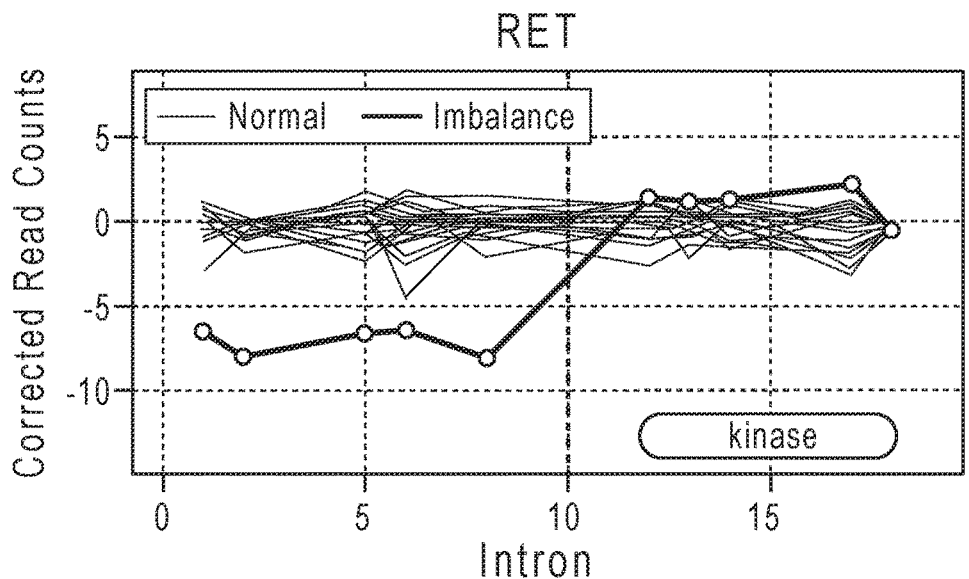
FIG. 22 shows an example of plots of the corrected read counts for the RET gene.
Figure 23:
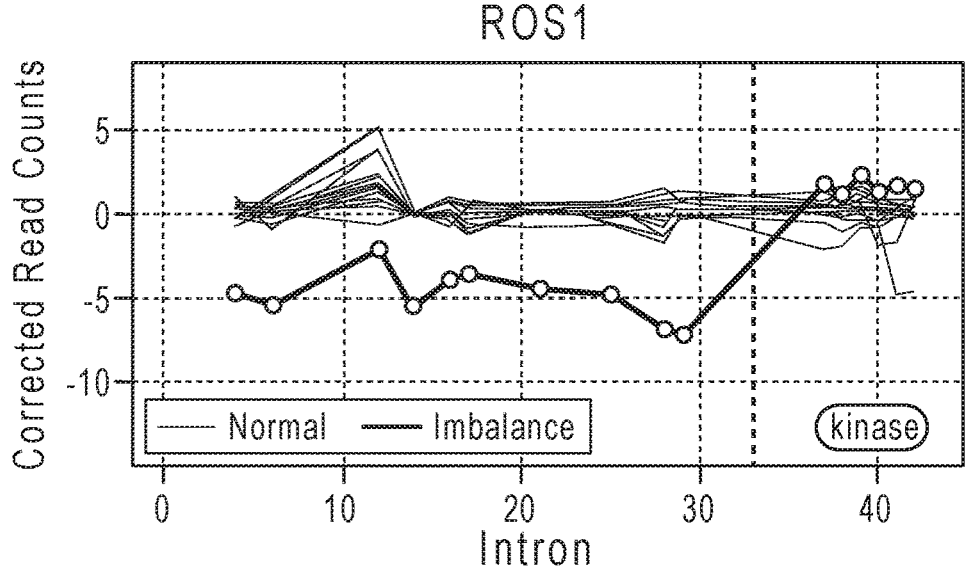
FIG. 23 shows an example of plots of the corrected read counts for the ROS1 gene.

FIG. 22 shows an example of plots of the corrected read counts for the RET gene. The imbalance score is 1.906 and the p-value is 0.0027. FIG. 23 shows an example of plots of the corrected read counts for the ROS1 gene. The imbalance score is 3.399 and the p-value is 6e-04. Both of these examples meet the threshold requirements for fusion imbalance detection.

Figure 24A:
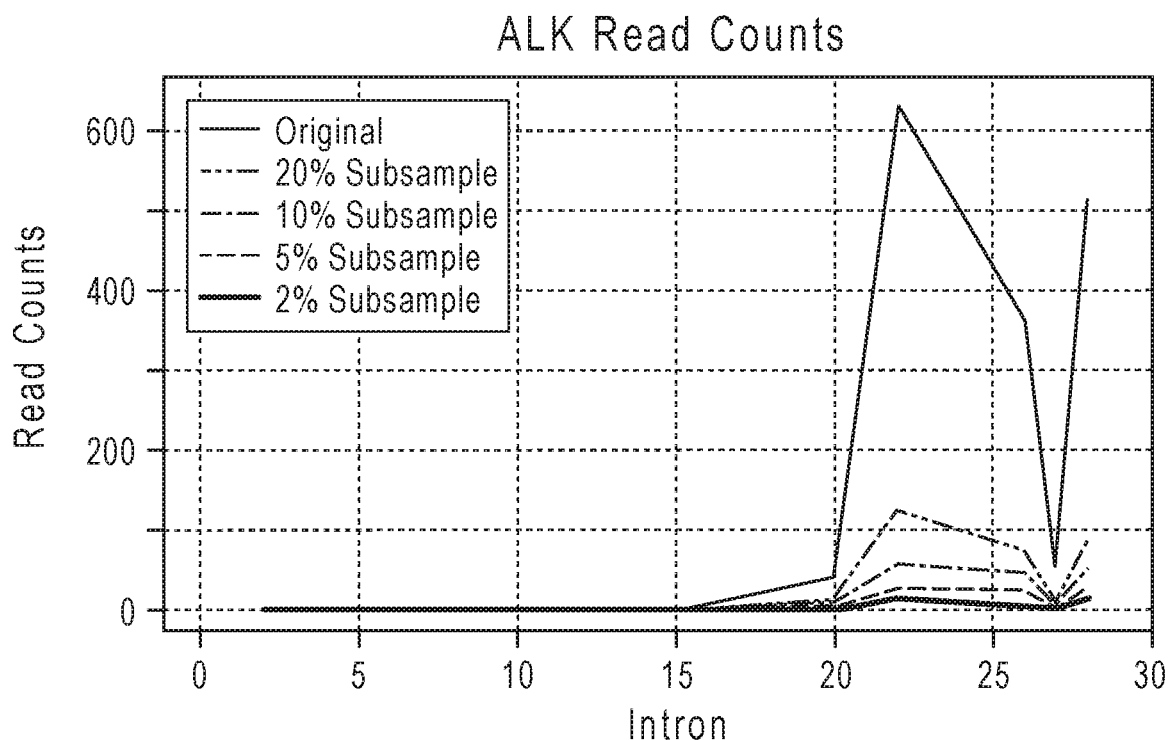
FIG. 24A shows examples of plots of read counts for original and reduced sets of read counts for the ALK gene.
Figure 24B:
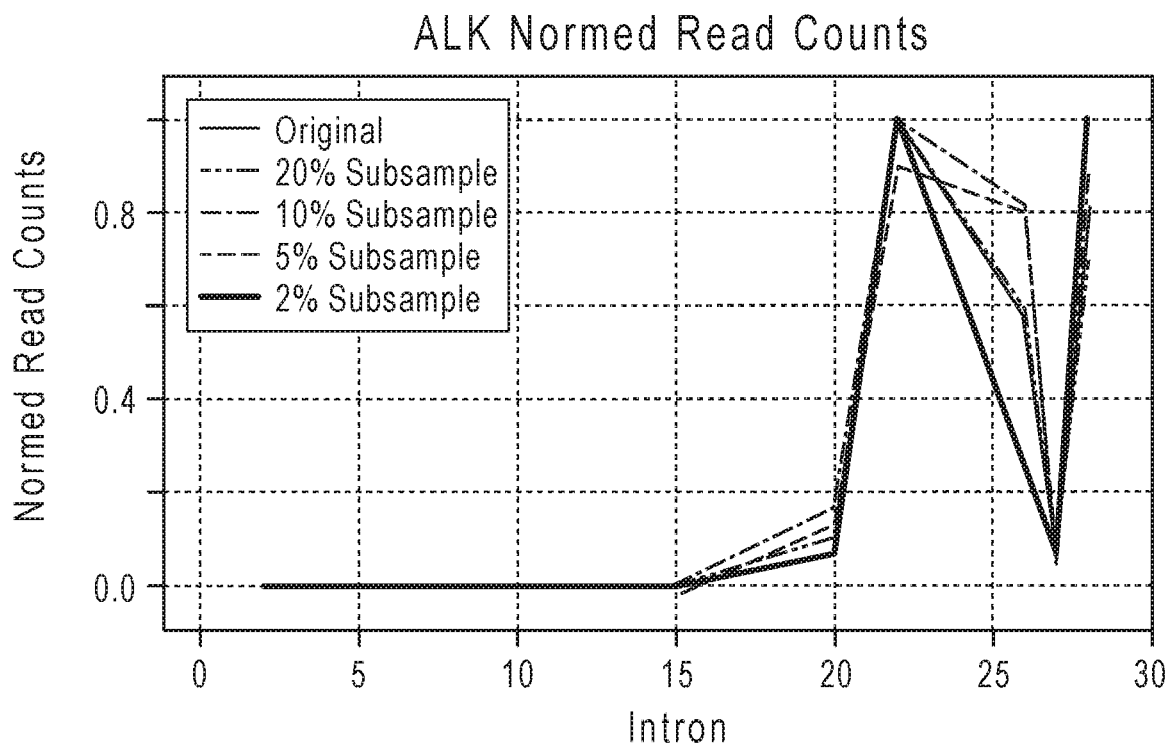
FIG. 24B shows examples of plots of normalized read counts for original and reduced sets of read counts for the ALK gene.
Figure 24C:
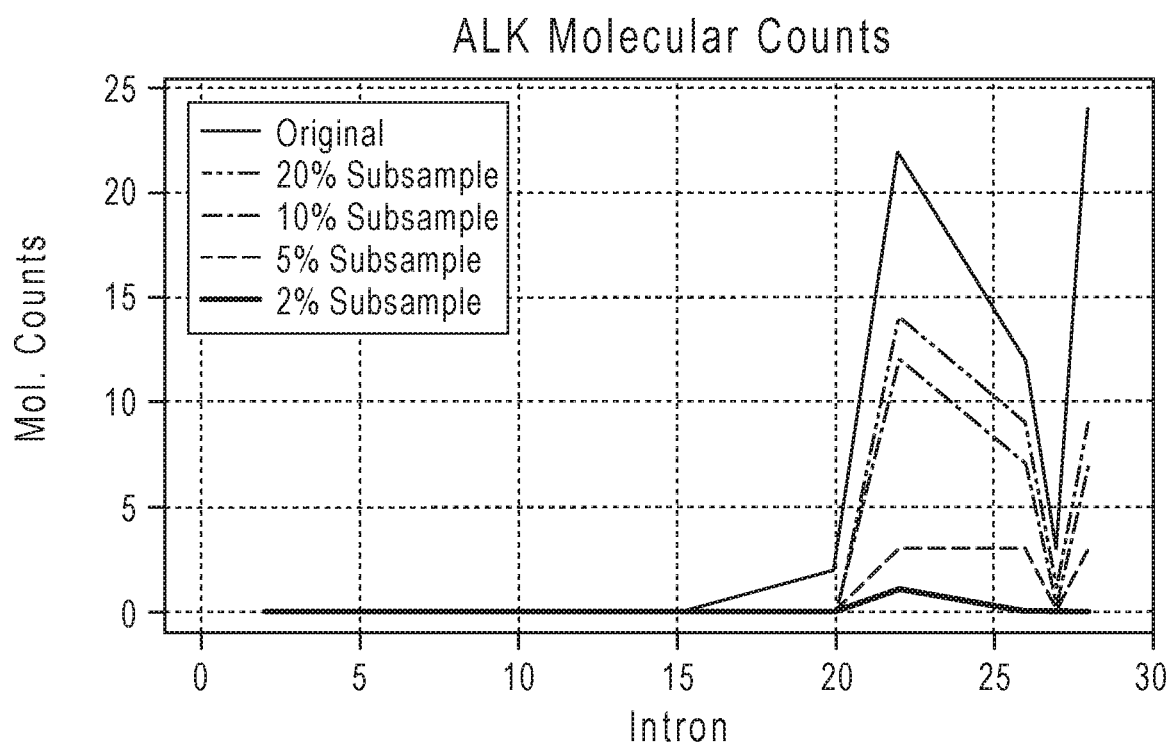
FIG. 24C shows examples of plots of molecular counts for original and reduced sets of molecular counts for the ALK gene.
Figure 24D:
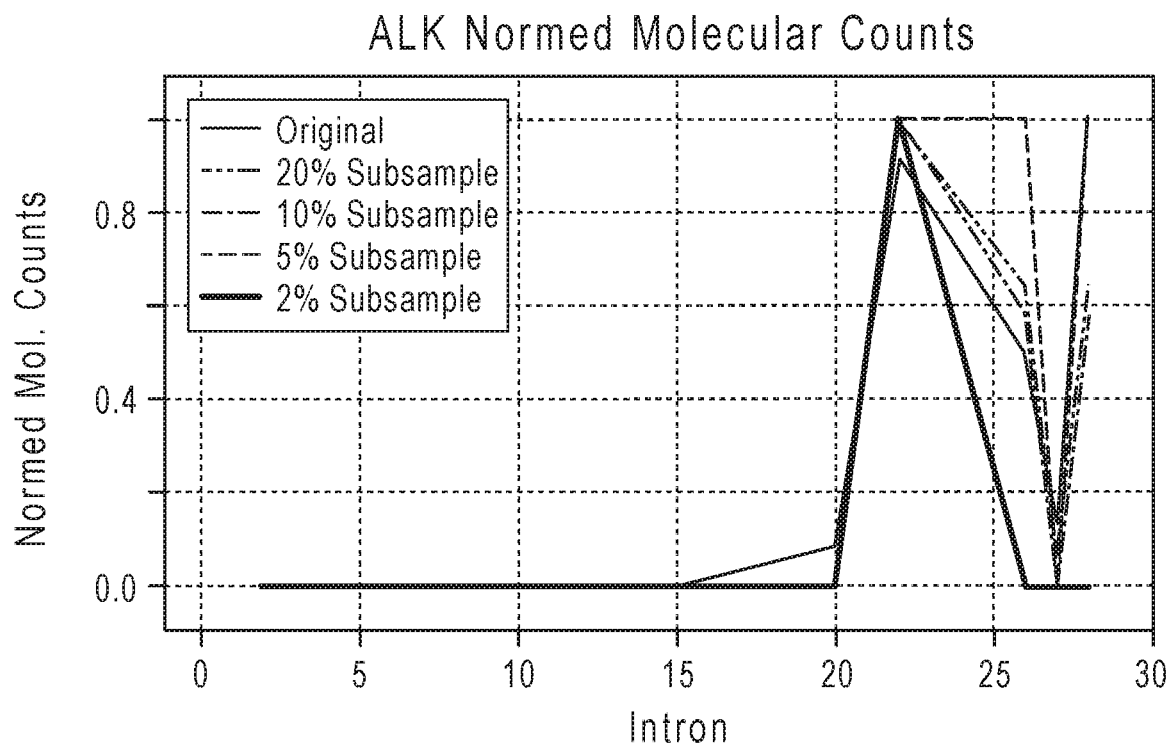
FIG. 24D shows examples of plots of normalized molecular counts for original and reduced sets of molecular counts for the ALK gene.

In some embodiments, the read counts or the molecular counts in the BAM file may be subsampled to a fraction of the original counts. For example, the fraction may range from 2% to 20% of the original counts. The subsampling may randomly select reads. The subsampled amplicons may be remapped and counted to form a reduced set of exon-tiling read counts or a reduced set of exon-tiling molecular counts. The imbalance analyses described in steps 1) to 7) can then be applied to the reduced set of exon-tiling read counts or the reduced set of exon-tiling molecular counts. FIGS. 24A-24D show examples of original and reduced sets of read counts for the ALK gene. The plots in FIGS. 24A and 24B give read counts and the plots in FIGS. 24C and 24D give molecular counts. These plots show that the coverage profiles are preserved when the reduced sets of reads are used. Table 5 shows examples of the results for exon tiling fusion imbalance for the reduced sets of reads. PPV is positive predictive value, FP is false positive, FN is false negative, and TP is true positive.

TABLE 5

| Subsampling | Total mapped reads | Exon Tiling (imbalance) |
| --- | --- | --- |
| Full run | 5,362,798 | Sensitivity = 75.0%<br>PPV = 92.3%<br>(1 FP; 4 FN; 12 TP) |
| 20% | 1,071,109 | Sensitivity = 75.0%<br>PPV = 92.3%<br>(1 FP; 4 FN; 12 TP) |
| 10% | 534,870 | Sensitivity = 81.2%<br>PPV = 100%<br>(0 FP; 3 FN; 13 TP) |
| 5% | 267,642 | Sensitivity = 81.2%<br>PPV = 100%<br>(0 FP; 3 FN; 13 TP) |
| 2% | 106,949 | Sensitivity = 68.7%<br>PPV = 100%<br>(0 FP; 5 FN; 11 TP) |

These results show that the reduced sets of reads can provide comparable performance in fusion imbalance detection. The subsampling also provides compression of the read data, as shown in Table 5's "Total mapped reads" column. The reduced sets of reads require less memory for storage. Furthermore, the reduced sets of reads require fewer computations for the imbalance analyses, since there are fewer reads to analyze. For implementations of the method on a computer, the memory savings and reduced computational load improve computing performance.

Figure 25:
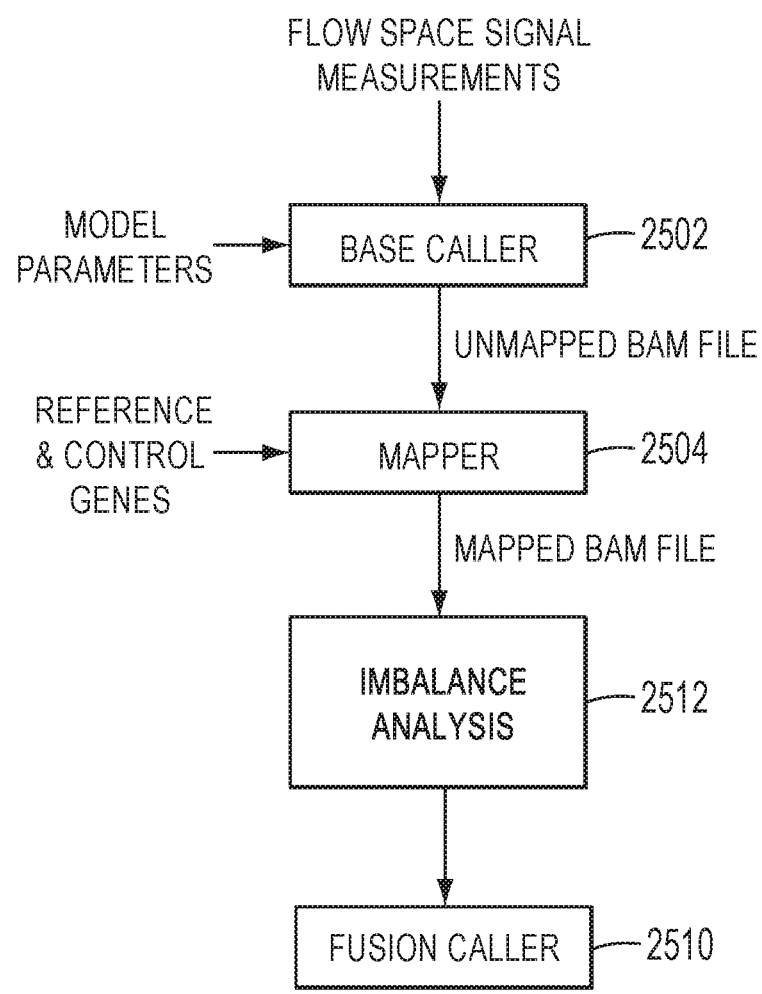
FIG. 25 is a block diagram of an exemplary method for detecting fusions based on imbalance analysis, in accordance with an embodiment.

FIG. 25 is a block diagram of an exemplary method for detecting fusions based on imbalance analysis, in accordance with an embodiment. Flow space signal measurements may be provided to a processor by a nucleic acid sequencing device. In some embodiments, each flow space signal measurement represents a signal amplitude or intensity measured in response to an incorporation or non-incorporation of a flowed nucleotide by sample nucleic acids in microwells of a sensor array. For an incorporation event, the signal amplitudes depend on the number of bases incorporated at one flow. For homopolymers, the signal amplitudes increase with increasing homopolymer length. The processor may apply a base caller 2502 to generate base calls for a sequence read by analyzing flow space signal measurements.

Figure 28:
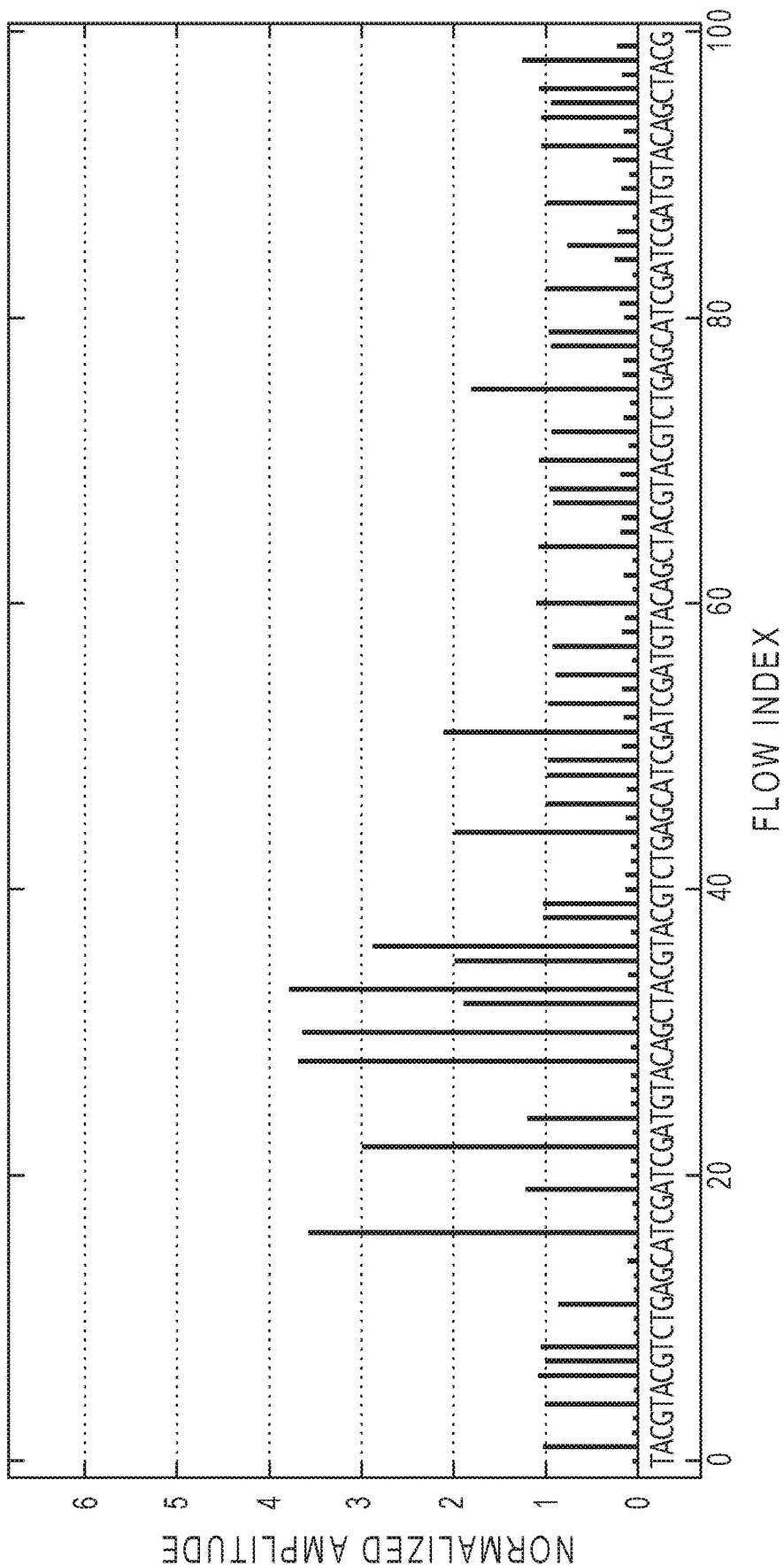
FIG. 28 shows an exemplary representation of flow space signal measurements from which base calls may be made.

FIG. 28 shows an exemplary representation of flow space signal measurements from which base calls may be made. In this example, the x-axis shows the flow index and the nucleotide that was flowed in a flow sequence. The bars in the graph show the amplitudes of the flow space signal measurements for each flow from a particular location of a microwell in the sensor array. The flow space signal measurements may be raw acquisition data or data having been processed, such as, e.g., by scaling, background filtering, normalization, correction for signal decay, and/or correction for phase errors or effects, etc. The base calls may be made by analyzing any suitable signal characteristics (e.g., signal amplitude or intensity). The structure and/or design of a sensor array, signal processing and base calling for use with the present teachings may include one or more features described in U.S. Pat. Appl. Publ. No. 2013/0090860, Apr. 11, 2013, incorporated by reference herein in its entirety.

Once the base sequence for the sequence read is determined, the sequence reads may be provided to mapper 2504, for example, in an unmapped BAM file. In some embodiments, the mapper 2504 aligns the sequence reads to a reference sequence including the targeted exon-exon junctions and control genes reference sequences to determine aligned sequence reads and associated mapping quality parameters. The reference sequence and control gene reference sequence may be provided in a file using the FASTA file format or another suitable file format. Methods for aligning sequence reads for use with the present teachings may include one or more features described in U.S. Pat. Appl. Publ. No. 2012/0197623, published Aug. 2, 2012, incorporated by reference herein in its entirety.

In some embodiments, the aligned sequence reads may be provided to the imbalance analysis pipeline 2512. The imbalance analysis pipeline 2512 may apply the steps 1) to 7) described above. The results of the thresholding applied to the imbalance score and the p-value to detect a driver gene fusion may be provided to the fusion caller 2510. The fusion caller 2510 may provide a fusion call based on the results of the thresholding applied in the imbalance analysis. In some embodiments, results of the imbalance call may be combined with results of a targeted isoform call when that information is available. An example of combining the imbalance calls with the targeted isoform calls to give a reported fusion call is given in Table 4, above. Methods for detecting a targeted fusion for use with the present teachings may include one or more features described in U.S. patent application Ser. No. 16/136,463, filed on Sep. 20, 2018, incorporated by reference herein in its entirety.

Figure 26:
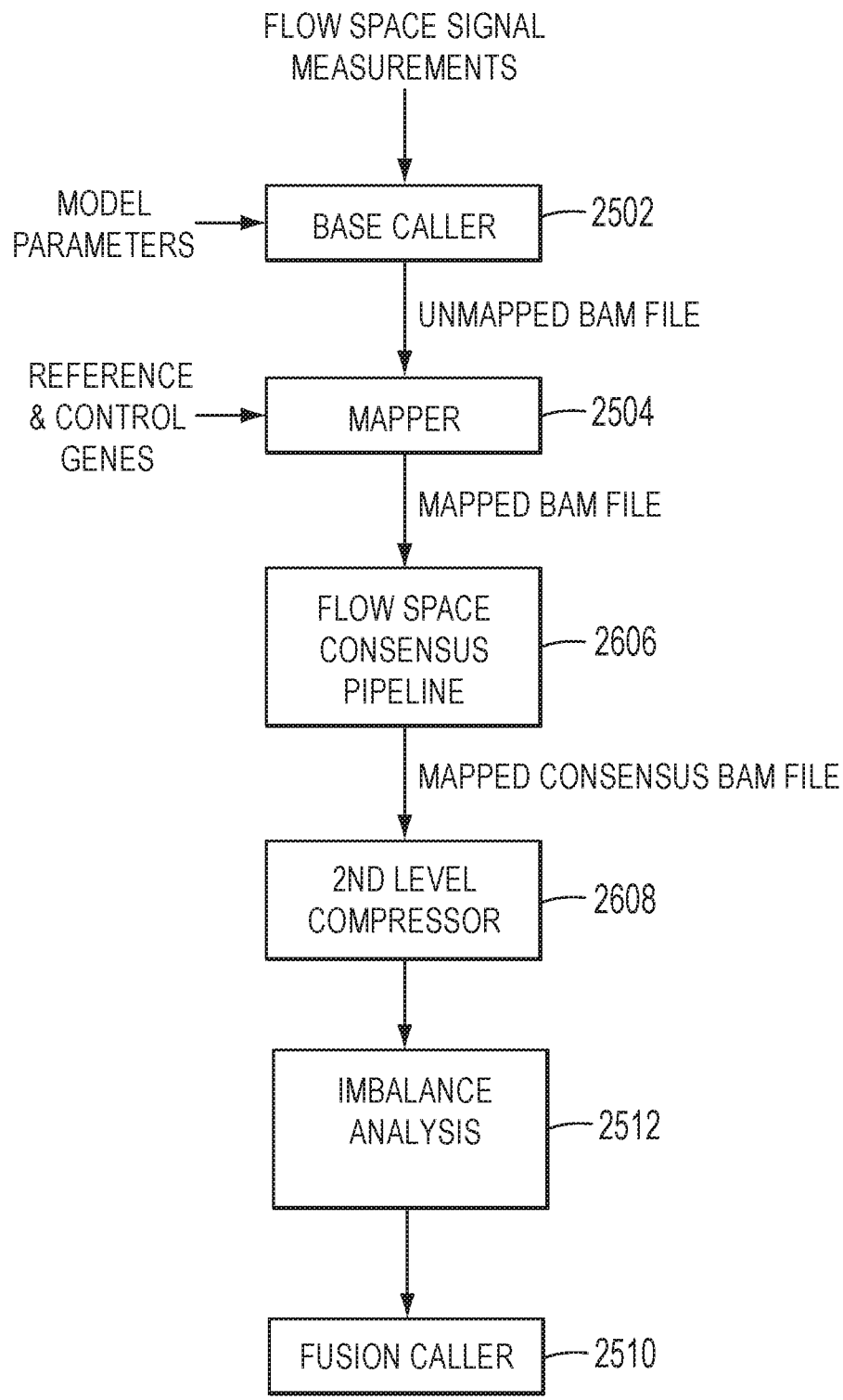
FIG. 26 is a block diagram of an exemplary method for generating consensus compressed data for detecting fusions based on imbalance analysis, in accordance with an embodiment.

In some embodiments, the sequence reads corresponding to exon-tiling amplicons include molecular tags. These sequence reads may be grouped into families sharing common molecular tags. The families may be counted for the amplicons corresponding to the exon-exon junctions to form molecular counts. FIG. 26 is a block diagram of an exemplary method for generating consensus compressed data for detecting fusions based on imbalance analysis, in accordance with an embodiment. The aligned sequence reads may be provided to the flow space consensus pipeline 2606, for example, in a mapped BAM file. A mapped consensus BAM file may be provided to a second level compressor 2608. The family counts, or molecular counts, may be provided to the imbalance analysis pipeline 2512. The imbalance analysis pipeline 2512 may apply the imbalance analysis method steps 1) to 7) to the molecular counts, or family counts, for exon-tiling amplicons instead of the read counts, or numbers of reads.

The BAM file format structure is described in "Sequence Alignment/Map Format Specification," Sep. 12, 2014 (https://github.com/samtools/hts-specs), referred to as "BAM specification" herein. As described herein, a "BAM file" refers to a file compatible with the BAM format. As described herein, an "unmapped" BAM file refers to a BAM file that does not contain aligned sequence read information or mapping quality parameters and a "mapped" BAM file refers to a BAM file that contains aligned sequence read information and mapping quality parameters. As described herein, a "consensus" BAM file refers to a BAM file that contains consensus compressed data.

In some embodiments, a read structure for a sequence read with molecular tagging may include, starting from the 5' end, a library key, a barcode sequence, a barcode adapter, a prefix molecular tag, a sequence template, a suffix molecular tag, and a P1 adapter. Base calling may include trimming the library key, barcode sequence and barcode adapter from the rest of the sequence read and storing them in the key sequence (KS) tag field of the read group header @RG of the BAM file format. Base calling may include trimming the P1 adapter from the sequence read and storing it in a comment line @CO of the BAM header.

In some embodiments, the base caller 2502 may be configured to detect the tag structure and trim the tag from the sequence read. Trimmed tags may be stored in the BAM read group header (@RG) in fields for custom tags ZT (for a prefix tag, for example) and YT (for a suffix tag, for example). Since the read group header is associated with the sequence read data of the template, the integrity of the tag's association with the family group may be maintained. Subsequent mapping or alignment with a reference sequence may be applied to the template sequence without a prefix tag or a suffix tag. This reduces the possibility of erroneous mapping of a portion of a tag to the reference sequence.

In some embodiments, a tag sequence may include a subset of random bases and a subset of known bases. A tag trimming method may require that the sequence of bases in the tag portion of the sequence read match the known bases. A tag trimming method may select a base string that has a number of bases equal to the known length of a tag. In some embodiments, a tag trimming method may detect and correct sequencing error in the tag, such as insertions and deletions. Correcting sequencing errors in the tag may provide more accurate family identification.

In some embodiments, the mapped BAM file may store a plurality of sequence reads, a plurality of vectors of flow space signal measurements and a plurality of sequence alignments corresponding to the sequence reads. The mapped BAM file may store the vectors of flow space signal measurements in the custom tag field ZM. The mapped BAM file may store the model parameters in the custom tag field ZP. The mapped BAM file may store the molecular tag sequences associated with the sequence reads in the BAM read group header, as described above. The mapped BAM file may be stored in memory and provided to the flow space consensus pipeline 2606. In some embodiments, other file formats may be used to store a plurality of sequence reads, a plurality of vectors of flow space signal measurements, a plurality of sequence alignments and molecular tag sequences corresponding to the sequence reads.

Figure 27:
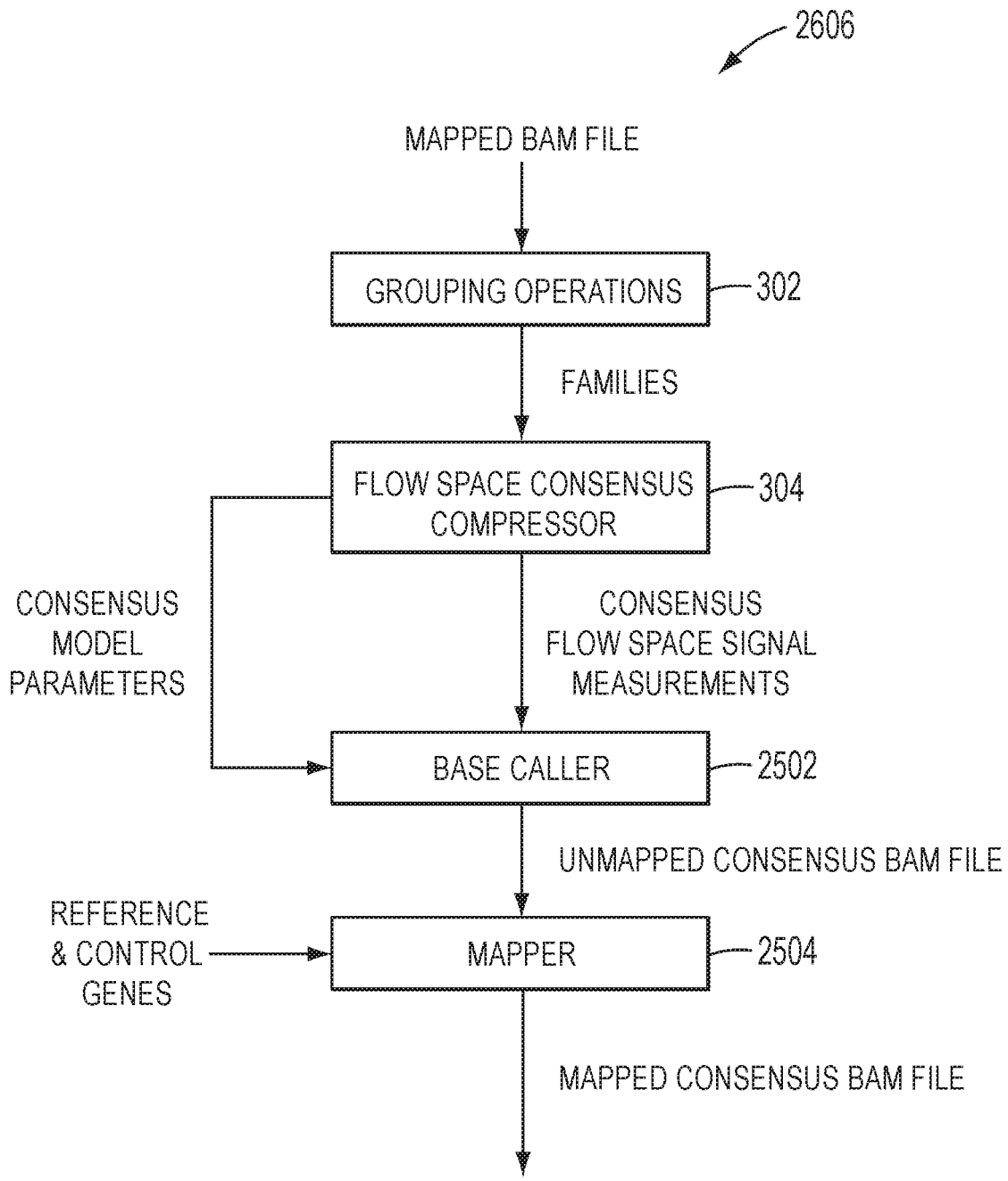
FIG. 27 is a block diagram of an exemplary method for the flow space consensus pipeline 2606, in accordance with an embodiment.

FIG. 27 is a block diagram of an exemplary method for the flow space consensus pipeline 2606, in accordance with an embodiment. Grouping operations 302 may use the molecular tag sequence information to identify families of sequence reads and corresponding flow space signal measurements. Grouping operations 302 may compare molecular tag sequences associated with the sequence reads and apply a grouping threshold. For example, the criterion of the grouping threshold can require that all tag sequences of members of a group of sequence reads have 100% tag sequence identity. Sequence reads and corresponding flow space signal measurements that are determined to share a common tag sequence, by meeting the criterion of the grouping threshold, are grouped into a given family, where the common tag sequence is unique to that family. Each family will have a number of members which is the number of sequence reads grouped in the family. In some embodiments, families not having at least a minimum number of members will not be further processed and may be removed from memory. Methods for grouping sequence reads based on molecular tag sequences for use with the present teachings may include one or more features described in U.S. Pat. Appl. Publ. No. 2016/0362748, published Dec. 15, 2016, incorporated by reference herein in its entirety.

In some embodiments, the flow space consensus compressor 304 may determine consensus compressed data based on the flow space signal measurements for each of the grouped families as follows:

A. Calculate an arithmetic mean of the vectors of flow space signal measurements of each grouped family to form a vector of consensus flow space signal measurements for each family.

B. Calculate a standard deviation of the vectors of flow space signal measurements of each family to form a vector of standard deviations for each family.

In some embodiments, the flow space consensus compressor 304 may receive at least one model parameter corresponding to each vector of flow space signal measurements. The flow space consensus compressor 304 may calculate an arithmetic mean of model parameters of the family to form at least one consensus model parameter for the family. The model parameters may be used for base calling, as described below. In some embodiments, the model parameters may include an incomplete extension (IE) parameter and a carry forward (CF) parameter for each vector of flow space signal measurements. The flow space consensus compressor 304 may calculate an arithmetic mean of the IE parameters and an arithmetic mean of the CF parameters of each family to form a consensus IE parameter and a consensus CF parameter for each family.

In some embodiments, the base caller 2502 may be applied to the vector of consensus flow space signal measurements for each family to generate a consensus base sequence for the respective family. A consensus base sequence is also referred to herein as a consensus sequence read. The consensus model parameters may be used in applying a model for base calling. For example, a consensus incomplete extension (IE) parameter and a consensus carry forward (CF) parameter for each family may be provided to the base caller 2502. The base calling may include one or more features described in U.S. Pat. Appl. Publ. No. 2013/0090860, published Apr. 11, 2013, and/or U.S. Pat. Appl. Publ. No. 2012/0109598, published May 3, 2012, which are all incorporated by reference herein in their entirety. A consensus sequence alignment for the consensus base sequence may be determined by comparing the consensus base sequence to the sequence read in the family having the highest mapping quality. If the consensus base sequence matches the sequence read having the highest mapping quality, the corresponding sequence alignment is selected as the consensus sequence alignment. If the consensus base sequence does not match the sequence read in the family having the highest mapping quality, the mapper 2504 may align the consensus base sequence to the targeted fusion reference sequence and control genes reference sequences to determine the consensus sequence alignment. Methods for aligning consensus sequence reads may include one or more features described in U.S. Pat. Appl. Publ. No. 2012/0197623, published Aug. 2, 2012, incorporated by reference herein in its entirety. In some embodiments, about 1% of consensus sequence reads, on average, may need realignment by the mapper 2504.

In some embodiments, the processor may store the consensus compressed data for each family in a compressed data structure in a memory. The consensus compressed data may include the consensus sequence read, the consensus sequence alignment, the vector of consensus flow space signal measurements, the vector of standard deviations and the number of members for each family. The consensus compressed data may further include a set of consensus model parameters for each family. If the family has been separated into subfamilies, the consensus compressed data may further include the consensus sequence read, the consensus sequence alignment, the vector of consensus flow space signal measurements, the vector of standard deviations and the number of members for each subfamily. In some embodiments, the compressed data structure may be compatible with the BAM file format to produce a mapped consensus BAM file. The BAM specification allows the user to define custom tag fields. For example, custom tag fields may be defined for the BAM file used to store some of the consensus compressed data, as shown in Table 6.

TABLE 6

| BAM Custom Tag Field | DATA |
|---|---|
| ZM | Consensus flow space signal measurements |
| ZP | Consensus model parameters |
| ZS | Standard deviations of flow space signal measurements |
| ZR | Number of sequence reads, or members, in family or subfamily |

The original sequence reads, original vectors of flow space signal measurements and original model parameters for each family are not included in the consensus compressed data and may be removed from memory. In some embodiments, the compressed data structure may use a different format protocol than the BAM file format, including custom file formats.

Figure 29:
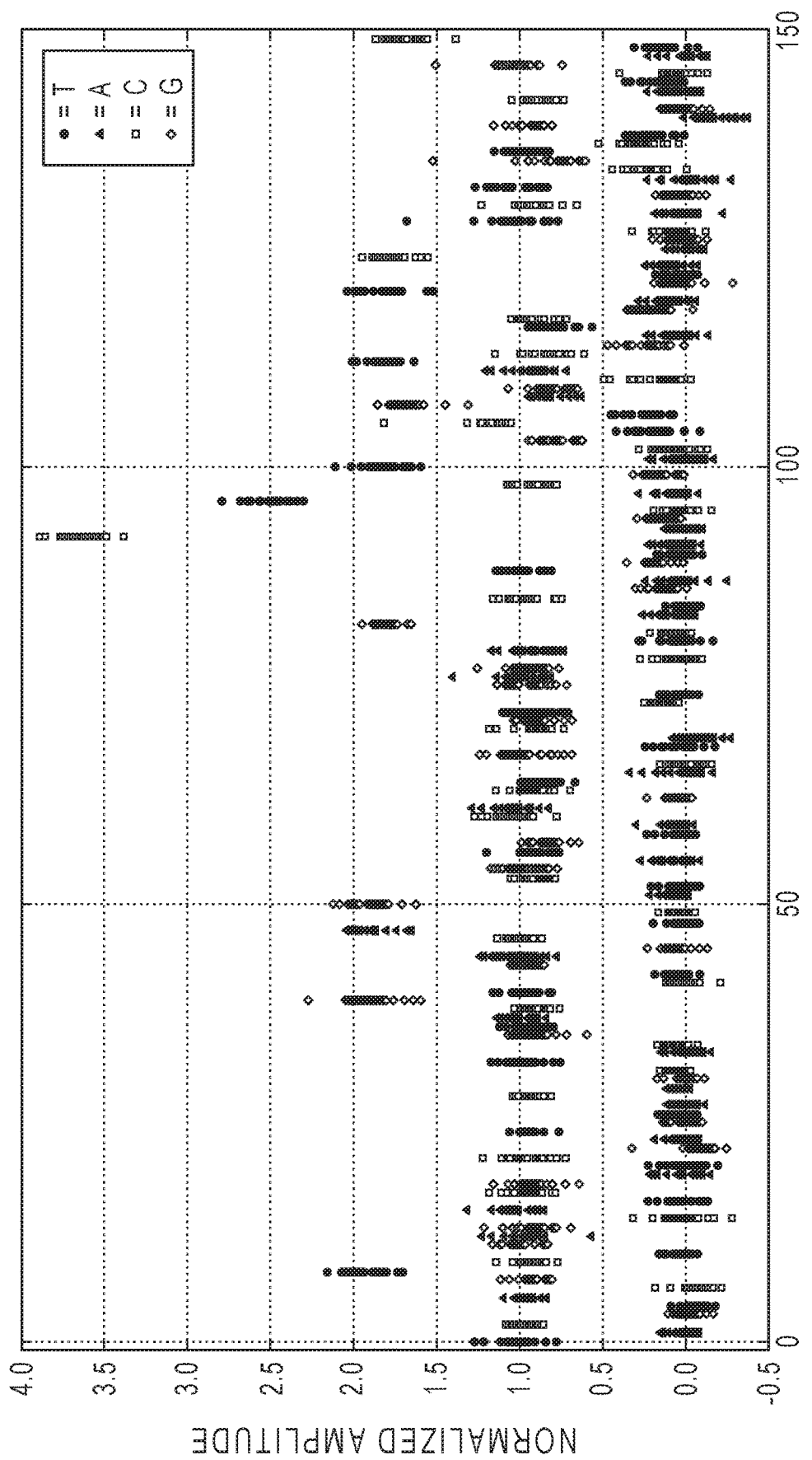
FIG. 29 illustrates an exemplary plot of flow space signal measurements for a single family. The flow index indicates the j-th flow in the flow sequence.

FIG. 29 illustrates an exemplary plot of flow space signal measurements for a single family. The flow index indicates the j-th flow in the flow sequence. The normalized amplitude indicates the value of the flow space signal measurement. The type of plot symbol corresponds to the nucleotide at the particular flow. This plot of flow space signal measurements corresponds to a single family of sequence reads associated with a common molecular tag. The values of the flow space signal measurements at each flow are clustered near similar values. The flow index corresponds to the element index in the vector of flow space signal measurements. The flow space signal measurements represented in this plot may be input to the flow space consensus compressor 304.

Figure 30:
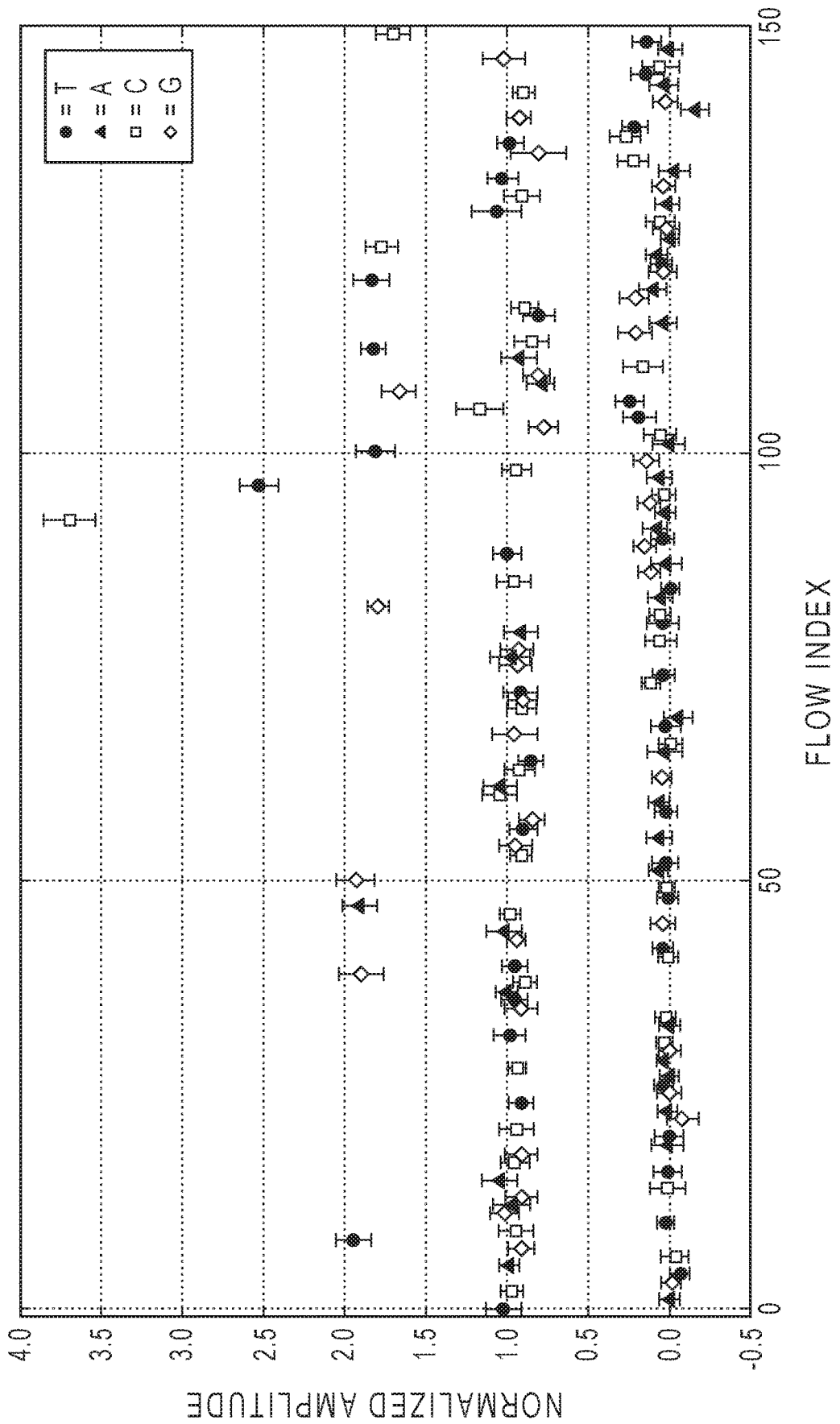
FIG. 30 illustrates an exemplary plot of consensus flow space signal measurements for a single family.

FIG. 30 illustrates an exemplary plot of consensus flow space signal measurements for a single family. This plot shows consensus flow space signal measurement values resulting from consensus calculations on the flow space signal measurements shown in FIG. 29. The plot symbols indicate the arithmetic means that are elements of the vector of consensus flow space measurements for the family. The bars indicate the standard deviations that are elements of the vector of standard deviations for the family.

For bidirectional sequencing, a first family may be designated for forward sequence reads and a second family may be designated for reverse sequence reads. The prefix and suffix tags of the forward read may be the reverse complement of the prefix and suffix tags for the reverse read, as shown in the example of Table 7.

TABLE 7

| Read Direction | Prefix Tag | Suffix Tag | Tag | Number of Sequence Reads |
|---|---|---|---|---|
| Forward Read | ACT | GGT | ACTGGT | 10 |
| Reverse Read | ACC | AGT | ACCAGT | 10 |
| Reverse Complement of Reverse Read Tags | GGT | ACT | ACTGGT | 20 |

In some embodiments, a family may be split into subfamilies, resulting in more than one consensus sequence read per family having the same molecular tags. Subfamilies may be formed for flow synchronization so that each subfamily has synchronized flow space signal measurements for determining the vector of consensus flow space measurements. A family may be split into subfamilies when there are variations in sequence reads within the family so that a consensus sequence read is generated for each subfamily. Methods for flow space consensus compression for molecular tagged nucleic acid sequence data for use with the present teachings may include one or more features described in U.S. patent application Ser. No. 15/979,804, filed May 15, 2018, incorporated by reference herein in its entirety.

Returning to FIG. 26, in some embodiments, a second level compressor 2608 may be applied to the consensus compressed data prior to fusions analysis. The second level compressor 2608 may combine the subfamilies having the same molecular tags into a single family that includes one consensus sequence read. In some embodiments for bidirectional sequencing reads, the second level compressor 2608 may combine the families for the forward and reverse sequence reads as follows:
1. Determine the reverse complement the prefix and suffix tags of the reverse reads to form a reverse complement tag,
2. Match the reverse complement tag with a forward read tag,
3. Combine the forward read family with the matching tag and the reverse read family into one family including one consensus sequence read.

Referring to Table 7, the number of reads represented by the combined family is the sum of numbers of sequence reads in the forward and reverse read families. The mapped consensus BAM file may be modified to include the combined family information and remove the subfamily information. The sum value may be entered in the ZR field of the mapped consensus BAM file. The second level compressor 2608 provides a single consensus sequence read for a combined family. By eliminating one subfamily's consensus sequence read for each combined family, the second level compressor 2608 provides additional data compression.

After second level compression, the consensus compressed data may be provided to the imbalance analysis pipeline 2512.

In some embodiments, the methods described herein may be performed or implemented at least partly using a distributed, clustered, remote, or cloud computing resource. Compression of the sequence read data to provide consensus compressed data provides advantages for transmitting the data to processors in a distributed, clustered, remote, or cloud computing resource. Since the volume of data is reduced, the bandwidth and/or time required for transmission across the data transfer interfaces between computing resources is reduced. For example, the mapped consensus BAM file may be transferred from a local computing resource to a cloud computing resource for fusion detection operations. The size of the mapped consensus BAM file would be significantly smaller than that of the original mapped BAM file. The smaller size of the mapped consensus BAM file would reduce the bandwidth and/or time required for transmission across a data transfer interface to the cloud computing resource.

According to an exemplary embodiment, there is provided a method for detecting a gene fusion, comprising (a) amplifying a nucleic acid sample in a presence of a primer pool to produce a plurality of amplicons, the primer pool including primers targeting a plurality of exon-exon junctions of a driver gene, wherein the amplicons correspond to the targeted exon-exon junctions; (b) sequencing the amplicons to generate a plurality of reads; (c) aligning the reads to a reference sequence, the reference sequence including nucleic acid sequences of the amplicons corresponding to the targeted exon-exon junctions of the driver gene; (d) determining a number of reads for each amplicon corresponding to each targeted exon-exon junction; (e) dividing the number of reads for each amplicon by a maximum number of reads among the amplicons of the driver gene to give a normalized read count for each amplicon; (f) applying a baseline correction to the normalized read counts for the amplicons to form corrected read counts, wherein the baseline correction uses baseline values based on read counts for amplicons of a plurality of normal samples; (g) determining an imbalance between the corrected read counts for the amplicons corresponding to a 5' end of the driver gene and the corrected read counts for the amplicons corresponding to a 3'end of the driver gene; and (h) detecting the gene fusion in the driver gene based on the imbalance. The step of determining an imbalance may further include calculating a partial sum, $S_i$ of the corrected read counts X from a first amplicon to an $i^{th}$ amplicon, where $S_i = X_1 + \ldots + X_i$ and calculating a sum $S_n$ of the corrected read counts from the first amplicon to an $n^{th}$ amplicon, where $S_n = X_1 + \ldots + X_n$, where n is a total number of corrected read counts. The step of determining an imbalance may further include determining a binary segmentation score, $Z_i$, for the $i^{th}$ amplicon by:

$$Z_i = \frac{\frac{S_i}{i} - \frac{S_n - S_i}{n-i}}{\sqrt{\frac{1}{i} + \frac{1}{n-1}}}$$

The step of determining an imbalance may further include determining a predicted breakpoint for the gene fusion based on an amplicon index corresponding to a maximum absolute binary segmentation score. The step of determining an imbalance may further include determining an imbalance score based on a ratio of an observed imbalance value and an expected imbalance value. The expected imbalance value may be based on a first array of the baseline values and the observed imbalance value may be based on a second array of the normalized read counts, wherein a number of array elements in each array is N. The step of determining an imbalance score may further include (a) calculating a first sum of the baseline values of the first array from an array element (1+b) to an array element N, where b is a predicted breakpoint; (b) calculating a second sum of the baseline values of the first array from an array element 1 to the array element N; and (c) dividing the first sum by the second sum to form the expected imbalance value. The step of determining an imbalance score may further include (a) calculating a first sum of the normalized read counts of the second array from an array element (1+b) to an array element N, where b is a predicted breakpoint; (b) calculating a second sum of the normalized read counts of the second array from an array element 1 to the array element N; and (c) dividing the first sum by the second sum to form the observed imbalance value. For the driver gene located at the 5' end, the step of determining an imbalance score may further include (a) calculating a first sum of the baseline values of the first array from an array element 1 to an array element b, where b is a predicted breakpoint; (b) calculating a second sum of the baseline values of the first array from an array element 1 to the array element N; and (c) dividing the first sum by the second sum to form the expected imbalance value. For the driver gene located at the 5' end, the step of determining an imbalance score may further include (a) calculating a first sum of the normalized read counts of the second array from an array element 1 to an array element b, where b is a predicted breakpoint; (b) calculating a second sum of the normalized read counts of the second array from an array element 1 to the array element N; and (c) dividing the first sum by the second sum to form the observed imbalance value. The baseline value for each amplicon may be a median value of a plurality of normalized read counts determined for the amplicon of the plurality of normal samples. The step of detecting the gene fusion may further include determining a p-value by applying a Wilcoxon rank test to compare a plurality of the binary segmentation scores to a second plurality of binary segmentation scores corresponding to a second plurality of amplicons of a control gene. The step of detecting the gene fusion may further include applying a threshold to the p-value. The step of detecting the gene fusion may further include applying a threshold to the imbalance score.

According to an exemplary embodiment, there is provided a system for detecting a gene fusion, comprising a machine-readable memory and a processor in communication with the memory, wherein the processor is configured to execute machine-readable instructions, which, when executed by the processor, cause the system to perform a method comprising (a) receiving, at the processor, a plurality of nucleic acid sequence reads for a plurality of amplicons produced by amplification of a nucleic acid sample a presence of a primer pool, the primer pool including primers targeting a plurality of exon-exon junctions of a driver gene, wherein the amplicons correspond to the exon-exon junctions; (b) aligning the reads to a reference sequence, the reference sequence including nucleic acid sequences of the amplicons corresponding to the targeted exon-exon junctions of the driver gene; (c) determining a number of reads for each amplicon corresponding to each targeted exon-exon junction; (d) dividing the number of reads for each amplicon by a maximum number of reads among the amplicons of the driver gene to give a normalized read count for each amplicon; (e) applying a baseline correction to the normalized read counts for the amplicons to form corrected read counts, wherein the baseline correction uses baseline values based on read counts for amplicons of a plurality of normal samples; (f) determining an imbalance between the corrected read counts for the amplicons corresponding to a 5' end of the driver gene and the corrected read counts for the amplicons corresponding to a 3'end of the driver gene; and (f) detecting the gene fusion in the driver gene based on the imbalance. The step of determining an imbalance may further include calculating a partial sum, $S_i$ of the corrected read counts X from a first amplicon to an $i^{th}$ amplicon, where $S_i = X_1 + \ldots + X_i$ and calculating a sum $S_n$ of the corrected read counts from the first amplicon to an $n^{th}$ amplicon, where $S_n = X_1 + \ldots + X_n$, where n is a total number of corrected read counts. The step of determining an imbalance may further include determining a binary segmentation score, $Z_i$, for the $i^{th}$ amplicon by:

$$Z_i = \frac{\frac{Si}{i} - \frac{Sn - Si}{n - i}}{\sqrt{\frac{1}{i} + \frac{1}{n-1}}}$$

The step of determining an imbalance may further include determining a predicted breakpoint for the gene fusion based on an amplicon index corresponding to a maximum absolute binary segmentation score. The step of determining an imbalance may further include determining an imbalance score based on a ratio of an observed imbalance value and an expected imbalance value. The expected imbalance value may be based on a first array of the baseline values and the observed imbalance value may be based on a second array of the normalized read counts, wherein a number of array elements in each array is N. The step of determining an imbalance score may further include (a) calculating a first sum of the baseline values of the first array from an array element (1+b) to an array element N, where b is a predicted breakpoint; (b) calculating a second sum of the baseline values of the first array from an array element 1 to the array element N; and (c) dividing the first sum by the second sum to form the expected imbalance value. The step of determining an imbalance score may further include (a) calculating a first sum of the normalized read counts of the second array from an array element (1+b) to an array element N, where b is a predicted breakpoint; (b) calculating a second sum of the normalized read counts of the second array from an array element 1 to the array element N; and (c) dividing the first sum by the second sum to form the observed imbalance value. For the driver gene located at the 5' end, the step of determining an imbalance score may further include (a) calculating a first sum of the baseline values of the first array from an array element 1 to an array element b, where b is a predicted breakpoint; (b) calculating a second sum of the baseline values of the first array from an array element 1 to the array element N; and (c) dividing the first sum by the second sum to form the expected imbalance value. For the driver gene located at the 5' end, the step of determining an imbalance score may further include (a) calculating a first sum of the normalized read counts of the second array from an array element 1 to an array element b, where b is a predicted breakpoint; (b) calculating a second sum of the normalized read counts of the second array from an array element 1 to the array element N; and (c) dividing the first sum by the second sum to form the observed imbalance value. The baseline value for each amplicon may be a median value of a plurality of normalized read counts determined for the amplicon of the plurality of normal samples. The step of detecting the gene fusion may further include determining a p-value by applying a Wilcoxon rank test to compare a plurality of the binary segmentation scores to a second plurality of binary segmentation scores corresponding to a second plurality of amplicons of a control gene. The step of detecting the gene fusion may further include applying a threshold to the p-value. The step of detecting the gene fusion may further include applying a threshold to the imbalance score.

According to an exemplary embodiment, there is provided a non-transitory machine-readable storage medium comprising instructions which, when executed by a processor, cause the processor to perform a method for detecting a gene fusion, comprising (a) receiving, at the processor, a plurality of nucleic acid sequence reads for a plurality of amplicons produced by amplification of a nucleic acid sample a presence of a primer pool, the primer pool including primers targeting a plurality of exon-exon junctions of a driver gene, wherein the amplicons correspond to the exon-exon junctions; (b) aligning the reads to a reference sequence, the reference sequence including nucleic acid sequences of the amplicons corresponding to the targeted exon-exon junctions of the driver gene; (c) determining a number of reads for each amplicon corresponding to each targeted exon-exon junction; (d) dividing the number of reads for each amplicon by a maximum number of reads among the amplicons of the driver gene to give a normalized read count for each amplicon; (e) applying a baseline correction to the normalized read counts for the amplicons to form corrected read counts, wherein the baseline correction uses baseline values based on read counts for amplicons of a plurality of normal samples; (f) determining an imbalance between the corrected read counts for the amplicons corresponding to a 5' end of the driver gene and the corrected read counts for the amplicons corresponding to a 3'end of the driver gene; and (f) detecting the gene fusion in the driver gene based on the imbalance. The step of determining an imbalance may further include calculating a partial sum, $S_i$ of the corrected read counts X from a first amplicon to an $i^{th}$ amplicon, where $S_i = X_1 + \ldots + X_i$ and calculating a sum $S_n$ of the corrected read counts from the first amplicon to an $n^{th}$ amplicon, where $S_n = X_1 + \ldots + X_n$, where n is a total number of corrected read counts. The step of determining an imbalance may further include determining a binary segmentation score, $Z_i$, for the $i^{th}$ amplicon by:

$$Z_i = \frac{\frac{Si}{i} - \frac{Sn - Si}{n - i}}{\sqrt{\frac{1}{i} + \frac{1}{n-1}}}$$

The step of determining an imbalance may further include determining a predicted breakpoint for the gene fusion based on an amplicon index corresponding to a maximum absolute binary segmentation score. The step of determining an imbalance may further include determining an imbalance score based on a ratio of an observed imbalance value and an expected imbalance value. The expected imbalance value may be based on a first array of the baseline values and the observed imbalance value may be based on a second array of the normalized read counts, wherein a number of array elements in each array is N. The step of determining an imbalance score may further include (a) calculating a first sum of the baseline values of the first array from an array element (1+b) to an array element N, where b is a predicted breakpoint; (b) calculating a second sum of the baseline values of the first array from an array element 1 to the array element N; and (c) dividing the first sum by the second sum to form the expected imbalance value. The step of determining an imbalance score may further include (a) calculating a first sum of the normalized read counts of the second array from an array element (1+b) to an array element N, where b is a predicted breakpoint; (b) calculating a second sum of the normalized read counts of the second array from an array element 1 to the array element N; and (c) dividing the first sum by the second sum to form the observed imbalance value. For the driver gene located at the 5' end, the step of determining an imbalance score may further include (a) calculating a first sum of the baseline values of the first array from an array element 1 to an array element b, where b is a predicted breakpoint; (b) calculating a second sum of the baseline values of the first array from an array element 1 to the array element N; and (c) dividing the first sum by the second sum to form the expected imbalance value. For the driver gene located at the 5' end, the step of determining an imbalance score may further include (a) calculating a first sum of the normalized read counts of the second array from an array element 1 to an array element b, where b is a predicted breakpoint; (b) calculating a second sum of the normalized read counts of the second array from an array element 1 to the array element N; and (c) dividing the first sum by the second sum to form the observed imbalance value. The baseline value for each amplicon may be a median value of a plurality of normalized read counts determined for the amplicon of the plurality of normal samples. The step of detecting the gene fusion may further include determining a p-value by applying a Wilcoxon rank test to compare a plurality of the binary segmentation scores to a second plurality of binary segmentation scores corresponding to a second plurality of amplicons of a control gene. The step of detecting the gene fusion may further include applying a threshold to the p-value. The step of detecting the gene fusion may further include applying a threshold to the imbalance score.

According to an exemplary embodiment, there is provided a method for detecting a gene fusion, comprising (a) amplifying a nucleic acid sample in a presence of a primer pool to produce a plurality of amplicons, the primer pool including primers targeting a plurality of exon-exon junctions of a driver gene, wherein the amplicons correspond to the exon-exon junctions; (b) sequencing the amplicons to generate a plurality of reads; (c) aligning the reads to a reference sequence; (d) normalizing a number of reads corresponding to each amplicon by dividing the number of reads by a maximum number of reads among the amplicons of the driver gene to give a normalized read count for each amplicon; (e) applying a baseline correction to the normalized read counts for the amplicons of the driver gene to form corrected read counts, wherein the corrected read count for the amplicon is determined by a log 2 of the normalized read count divided by a baseline value for the amplicon; (f) calculating a binary segmentation score for each corrected read count to provide a plurality of binary segmentation scores corresponding to the plurality of amplicons; and (g) determining a predicted breakpoint for the gene fusion based on an amplicon index corresponding to a maximum absolute binary segmentation score. The step of calculating a binary segmentation score may further include calculating a partial sum $S_i$ of the corrected read counts X from a first amplicon to an $i^{th}$ amplicon, where $S_i = X_1 + \ldots + X_i$ and calculating a sum $S_n$ of all the corrected read counts from the first amplicon to an $n^{th}$ amplicon, where $S_n = X_1 + \ldots + X_n$, where n is a total number of corrected read counts. The step of calculating a binary segmentation score may further include determining the binary segmentation score for the $i^{th}$ amplicon by:

$$Z_i = \frac{\frac{Si}{i} - \frac{Sn - Si}{n - i}}{\sqrt{\frac{1}{i} + \frac{1}{n-1}}}$$

The method may further include determining an imbalance score based on a ratio of an observed imbalance value and an expected imbalance value. The expected imbalance value may be based on an array of baseline normalized read counts, wherein a number of array elements in the array is N, and wherein the baseline normalized read counts correspond to amplicons of a normal sample. The step of determining an imbalance score may further include calculating a first sum of the baseline normalized read counts of the array from an array element (1+b) to an array element N, where b is the predicted breakpoint; calculating a second sum of the baseline normalized read counts of the array from an array element 1 to the array element N; and dividing the first sum by the second sum to form the expected imbalance value. The observed imbalance value may be based on an array of the normalized read counts, wherein a number of array elements in the array is N. The step of determining an imbalance score may further include calculating a first sum of the normalized read counts of the array from an array element (1+b) to an array element N, where b is the predicted breakpoint; calculating a second sum of the normalized read counts of the array from an array element 1 to the array element N; and dividing the first sum by the second sum to form the observed imbalance value. The method may further include determining the baseline value for the amplicon by calculating a median value of a plurality of normalized read counts for a corresponding amplicon in a plurality of normal samples. The method may further include determining a p-value by applying a Wilcoxon rank test to compare the plurality of binary segmentation scores to a second plurality of binary segmentation scores corresponding to a second plurality of amplicons of a control gene.

According to an exemplary embodiment, there is provided a system for detecting a gene fusion, comprising a machine-readable memory and a processor in communication with the memory, wherein the processor is configured to execute machine-readable instructions, which, when executed by the processor, cause the system to perform a method comprising (a) amplifying a nucleic acid sample in a presence of a primer pool to produce a plurality of amplicons, the primer pool including primers targeting a plurality of exon-exon junctions of a driver gene, wherein the amplicons correspond to the exon-exon junctions; (b) sequencing the amplicons to generate a plurality of reads; (c) aligning the reads to a reference sequence; (d) normalizing a number of reads corresponding to each amplicon by dividing the number of reads by a maximum number of reads among the amplicons of the driver gene to give a normalized read count for each amplicon; (e) applying a baseline correction to the normalized read counts for the amplicons of the driver gene to form corrected read counts, wherein the corrected read count for the amplicon is determined by a log 2 of the normalized read count divided by a baseline value for the amplicon; (f) calculating a binary segmentation score for each corrected read count to provide a plurality of binary segmentation scores corresponding to the plurality of amplicons; and (g) determining a predicted breakpoint for the gene fusion based on an amplicon index corresponding to a maximum absolute binary segmentation score. The step of calculating a binary segmentation score may further include calculating a partial sum $S_i$ of the corrected read counts X from a first amplicon to an $i^{th}$ amplicon, where $S_i = X_1 + \ldots + X_i$ and calculating a sum $S_n$ of all the corrected read counts from the first amplicon to an $n^{th}$ amplicon, where $S_n = X_1 + \ldots + X_n$, where n is a total number of corrected read counts. The step of calculating a binary segmentation score may further include determining the binary segmentation score for the $i^{th}$ amplicon by:

$$Z_i = \frac{\frac{Si}{i} - \frac{Sn - Si}{n - i}}{\sqrt{\frac{1}{i} + \frac{1}{n-1}}}$$

The method may further include determining an imbalance score based on a ratio of an observed imbalance value and an expected imbalance value. The expected imbalance value may be based on an array of baseline normalized read counts, wherein a number of array elements in the array is N, and wherein the baseline normalized read counts correspond to amplicons of a normal sample. The step of determining an imbalance score may further include calculating a first sum of the baseline normalized read counts of the array from an array element (1+b) to an array element N, where b is the predicted breakpoint; calculating a second sum of the baseline normalized read counts of the array from an array element 1 to the array element N; and dividing the first sum by the second sum to form the expected imbalance value. The observed imbalance value may be based on an array of the normalized read counts, wherein a number of array elements in the array is N. The step of determining an imbalance score may further include calculating a first sum of the normalized read counts of the array from an array element (1+b) to an array element N, where b is the predicted breakpoint; calculating a second sum of the normalized read counts of the array from an array element 1 to the array element N; and dividing the first sum by the second sum to form the observed imbalance value. The method may further include determining the baseline value for the amplicon by calculating a median value of a plurality of normalized read counts for a corresponding amplicon in a plurality of normal samples. The method may further include determining a p-value by applying a Wilcoxon rank test to compare the plurality of binary segmentation scores to a second plurality of binary segmentation scores corresponding to a second plurality of amplicons of a control gene.

According to an exemplary embodiment, there is provided a non-transitory machine-readable storage medium comprising instructions which, when executed by a processor, cause the processor to perform a method for detecting a gene fusion, comprising (a) amplifying a nucleic acid sample in a presence of a primer pool to produce a plurality of amplicons, the primer pool including primers targeting a plurality of exon-exon junctions of a driver gene, wherein the amplicons correspond to the exon-exon junctions; (b) sequencing the amplicons to generate a plurality of reads; (c) aligning the reads to a reference sequence; (d) normalizing a number of reads corresponding to each amplicon by dividing the number of reads by a maximum number of reads among the amplicons of the driver gene to give a normalized read count for each amplicon; (e) applying a baseline correction to the normalized read counts for the amplicons of the driver gene to form corrected read counts, wherein the corrected read count for the amplicon is determined by a log 2 of the normalized read count divided by a baseline value for the amplicon; (f) calculating a binary segmentation score for each corrected read count to provide a plurality of binary segmentation scores corresponding to the plurality of amplicons; and (g) determining a predicted breakpoint for the gene fusion based on an amplicon index corresponding to a maximum absolute binary segmentation score. The step of calculating a binary segmentation score may further include calculating a partial sum $S_i$ of the corrected read counts X from a first amplicon to an $i^{th}$ amplicon, where $S_i = X_1 + \ldots + X_i$ and calculating a sum $S_n$ of all the corrected read counts from the first amplicon to an $n^{th}$ amplicon, where $S_n = X_1 + \ldots + X_n$, where n is a total number of corrected read counts. The step of calculating a binary segmentation score may further include determining the binary segmentation score for the $i^{th}$ amplicon by:

$$Z_i = \frac{\frac{Si}{i} - \frac{Sn - Si}{n - i}}{\sqrt{\frac{1}{i} + \frac{1}{n-1}}}$$

The method may further include determining an imbalance score based on a ratio of an observed imbalance value and an expected imbalance value. The expected imbalance value may be based on an array of baseline normalized read counts, wherein a number of array elements in the array is N, and wherein the baseline normalized read counts correspond to amplicons of a normal sample. The step of determining an imbalance score may further include calculating a first sum of the baseline normalized read counts of the array from an array element (1+b) to an array element N, where b is the predicted breakpoint; calculating a second sum of the baseline normalized read counts of the array from an array element 1 to the array element N; and dividing the first sum by the second sum to form the expected imbalance value. The observed imbalance value may be based on an array of the normalized read counts, wherein a number of array elements in the array is N. The step of determining an imbalance score may further include calculating a first sum of the normalized read counts of the array from an array element (1+b) to an array element N, where b is the predicted breakpoint; calculating a second sum of the normalized read counts of the array from an array element 1 to the array element N; and dividing the first sum by the second sum to form the observed imbalance value. The method may further include determining the baseline value for the amplicon by calculating a median value of a plurality of normalized read counts for a corresponding amplicon in a plurality of normal samples. The method may further include determining a p-value by applying a Wilcoxon rank test to compare the plurality of binary segmentation scores to a second plurality of binary segmentation scores corresponding to a second plurality of amplicons of a control gene.

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 31:
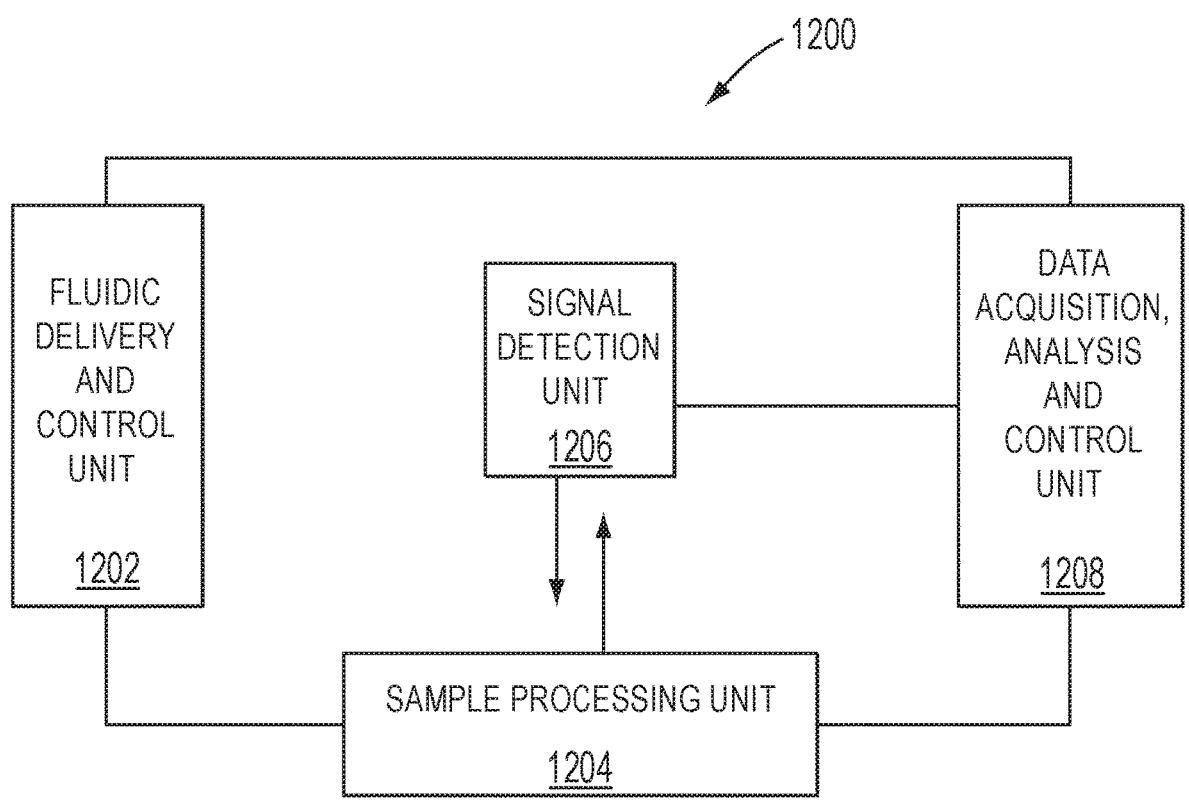
FIG. 31 shows a block diagram of a nucleic acid sequencing system, in accordance with various embodiments.

Various embodiments of nucleic acid sequencing platforms, such as a nucleic acid sequencer, can include components as displayed in the block diagram of FIG. 31. According to various embodiments, sequencing instrument 1200 can include a fluidic delivery and control unit 1202, a sample processing unit 1204, a signal detection unit 1206, and a data acquisition, analysis and control unit 1208. Various embodiments of instrumentation, reagents, libraries and methods used for next generation sequencing are described in U.S. Patent Application Publication No. 2009/0127589 and No. 2009/0026082. Various embodiments of instrument 1200 can provide for automated sequencing that can be used to gather sequence information from a plurality of sequences in parallel, such as substantially simultaneously.

In various embodiments, the fluidics delivery and control unit 1202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 1204 can include a sample chamber, such as flow cell, a substrate, a micro-array, a multi-well tray, or the like. The sample processing unit 1204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 1206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 1206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 1206 can include optics for the transmission of light from an illumination source to the sample or from the sample to the imaging or detection sensor. Alternatively, the signal detection unit 1206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 1208 can monitor various system parameters. The system parameters can include temperature of various portions of instrument 1200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 1200 can be used to practice variety of sequencing methods including ligation-based methods, sequencing by synthesis, single molecule methods, nanopore sequencing, and other sequencing techniques.

In various embodiments, the sequencing instrument 1200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 1200 can obtain the sequence information from a single nucleic acid molecule or from a group of substantially identical nucleic acid molecules.

In various embodiments, sequencing instrument 1200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory.

The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Those skilled in the art may appreciate from the foregoing description that the present teachings may be implemented in a variety of forms, and that the various embodiments may be implemented alone or in combination. Therefore, while the embodiments of the present teachings have been described in connection with particular examples thereof, the true scope of the embodiments and/or methods of the present teachings should not be so limited since other modifications will become apparent to the skilled practitioner upon a study of the drawings, specification, and following claims.

What is claimed is:

1. A method for detecting a gene fusion, comprising:
  amplifying a nucleic acid test sample in a presence of a primer pool to produce a plurality of amplicons, the primer pool including primers targeting a plurality of exon-exon junctions of a driver gene, wherein the amplicons correspond to the targeted exon-exon junctions;
  sequencing the amplicons to generate a plurality of reads;
  aligning the reads to a reference sequence, the reference sequence including nucleic acid sequences of the amplicons corresponding to the targeted exon-exon junctions of the driver gene;

determining a number of reads for each amplicon corresponding to each targeted exon-exon junction;

dividing the number of reads for each amplicon by a maximum number of reads among the amplicons of the driver gene to give a normalized read count for each amplicon;

determining a plurality of baseline values using a plurality of normalized read counts of corresponding amplicons obtained from a plurality of normal samples;

summing a portion of the baseline values for the amplicons corresponding to a portion of the driver gene in the plurality of normal samples to form a first sum;

dividing the first sum by a sum of the baseline values for the corresponding amplicons in the plurality of normal samples to form a first quotient;

summing a portion of the normalized read counts for the amplicons corresponding to the portion of the driver gene to form a second sum;

dividing the second sum by a sum of the normalized read counts for the test sample to form a second quotient;

calculating a ratio of the second quotient and the first quotient to produce an imbalance score; and detecting a presence or an absence of a gene fusion in the driver gene based on the imbalance score.

2. The method of claim 1, wherein the plurality of baseline values based on the normalized read counts for the corresponding amplicons of the plurality of normal samples provides values for a first array of and the plurality of normalized read counts for the nucleic acid test sample provides values for a second array, wherein a number of array elements in each of the first array and the second array is N.

3. The method of claim 2, wherein the summing a portion of the baseline values further comprises:
for the driver gene located at a 3' end,
calculating the first sum of the baseline values of the first array from an array element (1+b) to an array element N, where b is a predicted breakpoint.

4. The method of claim 2, wherein the summing a portion of the normalized read counts further comprises:
for the driver gene located at a 3' end,
calculating the second sum of the normalized read counts of the second array from an array element (1+b) to an array element N, where b is a predicted breakpoint.

5. The method of claim 2, wherein the summing a portion of the baseline values further comprises:
for the driver gene located at a 5' end,
calculating the first sum of the baseline values of the first array from an array element 1 to an array element b, where b is a predicted breakpoint.

6. The method of claim 2, wherein the summing a portion of the normalized read counts further comprises:
for the driver gene located at a 5' end,
calculating the second sum of the normalized read counts of the second array from an array element 1 to an array element b, where b is a predicted breakpoint.

7. The method of claim 1, wherein the step of determining a plurality of baseline values using a plurality of normalized read counts of corresponding amplicons obtained from a plurality of normal samples further comprises determining a median value of the normalized read counts for each of the corresponding amplicons of the plurality of normal samples, to form a corresponding one of the plurality of baseline values.

8. The method of claim 3, wherein the detecting a presence or an absence of a gene fusion further comprises determining a p-value by applying a Wilcoxon rank test to compare a plurality of the binary segmentation scores to a second plurality of binary segmentation scores corresponding to a second plurality of amplicons of a control gene.

9. The method of claim 8, wherein the threshold for the imbalance score is specific for a particular gene.

10. The method of claim 8, wherein the threshold for the imbalance score is adjustable by a user on a per-gene basis.

11. The method of claim 1, wherein the step of determining a plurality of baseline values using a plurality of normalized read counts of corresponding amplicons obtained from a plurality of normal samples further comprises determining a mean value of the normalized read counts for each of the corresponding amplicons of the plurality of normal samples, to form a corresponding one of the plurality of baseline values.

12. The method of claim 1, wherein the steps of amplifying, sequencing, aligning, determining a number of reads, and dividing the number of reads for each amplicon by a maximum number of reads are applied to the plurality of normal samples to generate the plurality of normalized read counts of corresponding amplicons for the step of determining a plurality of baseline values.

13. The method of claim 1, further comprising dividing the normalized read counts for the amplicons by the baseline values for the corresponding amplicons of the plurality of normal samples to form corrected read counts.

14. The method of claim 13, further comprising: calculating a partial sum, $S_i$, of the corrected read counts, X, from a first amplicon to an $i^{th}$ amplicon, where $S_i = X^0 \ldots + X$; and calculating a sum, S, of the corrected read counts from the first amplicon to an $n^{th}$ amplicon, where $Sn = X+ \ldots +X$, where n is a total number of corrected read counts.

15. The method of claim 14, further comprising determining a binary segmentation score, $Z_i$, for the i'h amplicon by:

$$z_i = \frac{\frac{S_i}{i} - \frac{Sn - Si}{n - i}}{\sqrt{\frac{1}{i} + \frac{1}{n-1}}''}$$

16. The method of claim 15, further comprising determining a predicted breakpoint for the gene fusion based on an amplicon index corresponding to a maximum absolute binary segmentation score.

17. The method of claim 15, wherein the detecting a presence or an absence of a gene fusion further comprisies determining a p-value by applying a Wilcoxon rank test to compare a plurality of the binary segmentation scores to a second plurality of binary segmentation scores corresponding to a second pllurality of amplicons of a control gene.

18. The method of claim 17, wherein the detecting a presence or an absence of a gene fusion further comprises applying a threshold to the p-value.

19. The method of claim 18, wherein the threshold for the p-value is specific for a particular gene.

20. The method of claim 18, wherein the threshold for the p-value is adjustable by a user on a per-gene basis.

* * * * *

UNITED STATES PATENT AND TRADEMARK OFFICE
CERTIFICATE OF CORRECTION

PATENT NO.           : 12,139,753 B2
APPLICATION NO.      : 16/825238
DATED                : November 12, 2024
INVENTOR(S)          : Rajesh Gottimukkala et al.

Page 1 of 2

It is certified that error appears in the above-identified patent and that said Letters Patent is hereby corrected as shown below:

In the Claims

In Column 36, Claim 8, Lines 1-6, delete "The method of claim 3, ......... of a control gene." and insert -- The method of claim 1, wherein the detecting a presence or an absence of a gene fusion further comprises applying a threshold to the imbalance score. --, therefor.

In Column 36, Claim 14, Line 32, delete "S,," and insert -- $S_i$, --, therefor.

In Column 36, Claim 14, Line 33, delete "i$^{th}$"" and insert -- $i^{th}$ --, therefor.

In Column 36, Claim 14, Line 33, delete "S," and insert -- $S_i$ --, therefor.

In Column 36, Claim 14, Line 33, delete "X$^o$"" and insert -- $X_1+$ --, therefor.

In Column 36, Claim 14, Line 33, delete "X;" and insert -- $X_i$; --, therefor.

In Column 36, Claim 14, Line 34, delete "S," and insert -- $S_n$, --, therefor.

In Column 36, Claim 14, Line 35, delete "n$^{th}$"" and insert -- $n^{th}$ --, therefor.

In Column 36, Claim 14, Line 35, delete "Sn" and insert -- $S_n$ --, therefor.

In Column 36, Claim 14, Line 35, delete "X+" and insert -- $X_1+$ --, therefor.

In Column 36, Claim 14, Line 33, delete "X," and insert -- $X_n$, --, therefor.

In Column 36, Claim 15, Line 39, delete "Z,," and insert -- $Z_i$, --, therefor.

In Column 36, Claim 15, Line 39, delete "i'h" and insert -- $i^{th}$ --, therefor.

Signed and Sealed this
Fourth Day of March, 2025

Coke Morgan Stewart
*Acting Director of the United States Patent and Trademark Office*

CERTIFICATE OF CORRECTION (continued)
U.S. Pat. No. 12,139,753 B2

In Column 36, Claim 17, Line 54, delete "comprisies" and insert -- comprises --, therefor.

In Column 36, Claim 17, Line 58, delete "pllurality" and insert -- plurality --, therefor.